United States Patent [19]

Kesseler et al.

[11] Patent Number: 4,925,852
[45] Date of Patent: May 15, 1990

[54] 3-DEMETHYLMEVALONIC ACID DERIVATIVES, AND PHARMACEUTICAL PRODUCTS BASED ON THESE COMPOUNDS

[75] Inventors: Kurt Kesseler, Bad Soden am Taunus; Gerhard Beck, Frankfurt am Main; Wilhelm Bartmann, Bad Soden am Taunus; Ernold Granzer, Kelkheim, all of Fed. Rep. of Germany

[73] Assignee: Hoechst Aktiengesellschaft, Frankfurt am Main, Fed. Rep. of Germany

[21] Appl. No.: 216,458

[22] Filed: Jul. 8, 1988

[30] Foreign Application Priority Data

Jul. 10, 1987 [DE] Fed. Rep. of Germany ........ 3722808

[51] Int. Cl.$^5$ .................... A61K 31/44; C07D 213/00; C07D 413/00; C07D 213/55
[52] U.S. Cl. .................................. 514/333; 514/277; 514/334; 514/336; 514/357; 514/269; 544/333; 544/335; 546/256; 546/257; 546/258; 546/283; 546/284; 546/335; 546/341; 546/342; 546/268
[58] Field of Search ............... 546/256, 268, 283, 284, 546/257, 258, 335, 341, 342, 268; 514/277, 333, 334, 336, 357

[56] References Cited

FOREIGN PATENT DOCUMENTS

| 0306929 | 3/1989 | European Pat. Off. ............ 546/256 |
| 0308736 | 3/1989 | European Pat. Off. ............ 546/256 |
| 0325130 | 7/1989 | European Pat. Off. ............ 546/256 |
| 0330057 | 8/1989 | European Pat. Off. ............ 546/256 |

OTHER PUBLICATIONS

Stokker et al., "Journal of Medicinal Chemistry", vol. 28, No. 3, 1985, pp. 347–358.

Primary Examiner—Mary C. Lee
Assistant Examiner—J. Richter
Attorney, Agent, or Firm—Finnegan, Henderson, Farabow, Garrett and Dunner

[57] ABSTRACT

3-Demethylmevalonic acid derivatives of the formula I (δ-lactone) and II (corresponding dihydroxy carboxylic acid derivative)

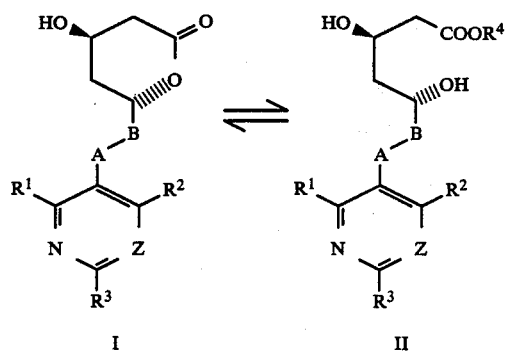

in which A—B, Z, $R^1$, $R^2$, $R^3$ and $R^4$ have the indicated meanings, a process for the preparation of these compounds, their use as medicaments, and pharmaceutical products, are described. In addition, new intermediates for the preparation of the compounds of the formula I and formula II are described.

9 Claims, No Drawings

3-DEMETHYLMEVALONIC ACID DERIVATIVES, AND PHARMACEUTICAL PRODUCTS BASED ON THESE COMPOUNDS

Derivatives of 3-hydroxy-3-methylglutaric acid (HMG) and of mevalonic acid have been described as inhibitors of cholesterol biosynthesis (M. T. Boots et al., J. Pharm. Sci. 69, 306 (1980), F. M. Singer et al., Proc. Soc. Exper. Biol. Med. 102, 270 (1959), H. Feres, Tetrahedron Lett. 24, 3769 (1983)). 3-Hydroxy-3-methylglutaric acid itself shows a significant cholesterol-lowering action in the rat and in human experiments (Z. Beg, Experimentia 23, 380 (1967), ibid 24, 15 (1968), P. J. Lupien et al., Lancet 1978, 1, 283).

Endo et al. (FEBS Letters 72, 323 (1976), J. Biol. Chem. 253, 1121 (1978)) reported the inhibition of 3-hydroxy-3-methylglutaryl-coenzyme A reductase (HMG-CoA reductase), the rate-determining enzyme of cholesterol biosynthesis, by the fermentation product "compactin".

Brown et al. (J. Chem. Soc. 1165 (1976) determined the chemical structure and the absolute configuration of "compactin" by a combination of chemical, spectroscopic and X-ray crystallographic methods and were able to show that "compactin" is a derivative of the lactone of 3-demethylmevalonic acid.

Compactin derivatives which inhibit the activity of HMG-CoA reductase have already been described (G. E. Stokker et al., J. Med. Chem. 28, 347-358 (1985)).

The present invention relates to new synthetic analogs of "compactin" in the form of the δ-lactone of the formula I or in the form of the dihydroxy acid derivative II

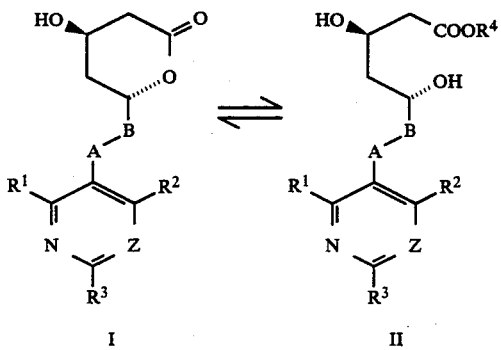

In the formulae
A—B denotes a radical of the formula —CH=CH— or —CH$_2$—CH$_2$—,
Z denotes a radical of the formula —CH or a nitrogen atom,
R$^1$, R$^2$ and R$^3$, independently of one another, denote hydrogen, a saturated or unsaturated, straight-chain or branched hydrocarbon radical which has up to 6 carbon atoms and can optionally be substituted on the terminal carbon by a saturated or unsaturated, cyclic hydrocarbon radical having 3-6 carbon atoms, a cyclic hydrocarbon radical which has 3-7 carbon atoms and is saturated or is unsaturated once or twice, an aromatic radical selected from the group comprising phenyl, furyl, thienyl or pyridinyl, which can optionally carry in the nucleus 1-3 identical or different substituents from the following groups: halogen, trifluoromethyl, alkyl or alkenyl, each having up to 6 carbon atoms, hydroxyl, alkoxy having 1-6 carbon atoms, carboxyl, or carbalkoxy having 1-6 carbon atoms in the alkoxy moiety, R$^4$ denotes hydrogen, a straight-chain or branched, saturated or unsaturated hydrocarbon radical having up to 5 carbon atoms, a benzyl radical whose nucleus can be substituted 1-2 times by halogen or an alkyl radical having 1-4 carbon atoms, an alkali metal or an ammonium ion NR$^5$R$^6$R$^7$R$^8$, where R$^{R5}$, R$^6$, R$^7$ and R$^8$ are identical or different and denote hydrogen, alkyl having 1-4 carbon atoms or hydroxyalkyl having 1-4 carbon atoms.

The invention relates to the pure enantiomers having the absolute configuration 4R,6S indicated in the general formula I or the absolute configuration 3R,5S depicted in formula II.

Preferred substituents R$^1$ and R$^2$ are a straight-chain or branched alkyl radical having 1-4 carbon atoms, a cycloalkyl radical having 3-6 carbon atoms, a cycloalkylmethyl or cycloalkenylmethyl radical having a ring size of 5-6 carbon atoms, a phenyl radical which can optionally carry 1-3 identical or different substituents from the following groups halogen, trifluoromethyl, alkyl having 1-4 carbon atoms, hydroxyl, alkoxy having 1-4 carbon atoms or carbalkoxy having 1-4 carbon atoms in the alkoxy moiety.

The preferred meanings for R$^3$ are hydrogen, a straight-chain or branched alkyl or alkenyl radical having up to 6 carbon atoms, a cycloalkyl or cycloalkenyl radical, each having 3-6 carbon atoms, a phenyl or pyridinyl radical, it being possible for the aromatic radicals optionally to carry 1-3 identical or different substituents from the following groups: halogen, alkyl having 1-4 carbon atoms, hydroxyl, alkoxy having 1-4 carbon atoms or carbalkoxy having 1-4 carbon atoms in the alkoxy moiety.

The preferred radicals R$^4$ are hydrogen, methyl, ethyl, isopropyl, isobutyl, benzyl, sodium, potassium, ammonium (NH$_4$) or methyltris(hydroxymethyl)ammonium.

Particularly preferred substituents R$^1$ are: methyl, ethyl, isopropyl, sec.-butyl, tert.-butyl, cyclopropyl, cyclohexyl, phenyl, 4-chlorophenyl, 4-fluorophenyl, 4-hydroxyphenyl, 4-methoxyphenyl, 4-fluoro-3-methylphenyl, 3,5-dimethylphenyl, cyclohexylmethyl and 4-trifluoromethylphenyl.

Particularly preferred substituents R$^2$ are methyl, ethyl, isopropyl, sec.-butyl, tert.-butyl, cyclopropyl, cyclohexyl, phenyl, 4-chlorophenyl, 4-fluorophenyl, 4-hydroxyphenyl, 4-methoxyphenyl, 4-fluoro-3-methylphenyl, 3,5-dimethylphenyl, cyclohexylmethyl and 4-trifluoromethylphenyl.

Particularly preferred substituents R$^3$ are hydrogen, methyl, isopropyl, tert.-butyl, cyclohexyl, phenyl, 4-fluorophenyl, 4-hydroxyphenyl, 2,5-dimethylphenyl, 3,5-dimethylphenyl and 4-trifluoromethylphenyl.

Particularly preferred substituents R$^4$ are hydrogen, methyl, ethyl, sodium and potassium.

Very particular preference is given to compounds of the formula I in which Z denotes a radical of the formula —CH or N, R$^1$ denotes ethyl, isopropyl, cyclopropyl, R$^2$ denotes 4-fluorophenyl, 4-hydroxyphenyl and R$^3$ denotes isopropyl, tert.-butyl, cyclohexyl, phenyl, 4-hydroxyphenyl or 4-fluorophenyl, and to the sodium and potassium salts of the corresponding dihydroxy carboxylic acids of the formula II.

The invention also relates to a process for the preparation of compounds of the formulae I and II, which comprises (a) reaction of the phosphonium salts of the formula III

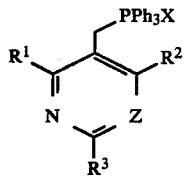

in which $R^1$, $R^2$, $R^3$ and Z have the meaning indicated for formula I, and X is Cl, Br or I, with the chiral aldehyde of the formula IV

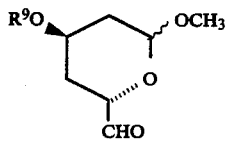

in which $R^9$ is a protective group which is stable to bases and weak acids, for example the $t\text{-}C_4H_9(C_6H_5)_2Si$ group, to give a compound of the formula V

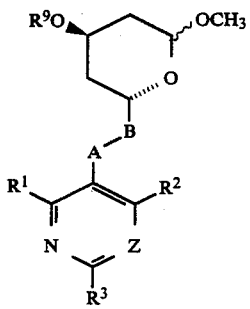

in which $R^1$, $R^2$, $R^3$ and Z have the meaning given for formula I, $R^9$ has the meaning given for formula IV, and A-B represents the (—CH=CH—) group, (b) acid hydrolysis of the methyl acetal group in a compound of the general formula V to give a lactol of the formula VI

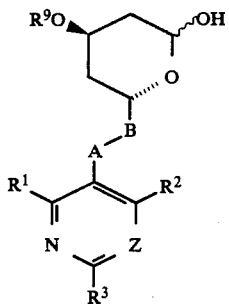

in which $R^1$, $R^2$, $R^3$ and Z have the meaning given for formula I, $R^9$ has the meaning given for formula IV, and A-B represents the (—CH=CH—) group, (c) oxidation of the compound of the formula VI to give a lactone of the general formula VII

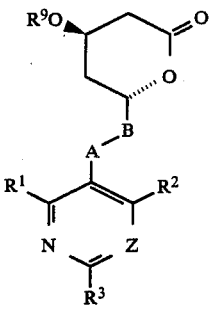

in which $R^1$, $R^2$, $R^3$ and Z have the meaning given for formula I, $R^9$ has the meaning given for formula IV, and A-B represents the (—CH=CH—) group, (d) elimination of the protective group $R^9$ in a compound of the general formula VII to give a compound of the formula I in which $R^1$, $R^2$, $R^3$ and Z have the meaning indicated for formula I, and A-B represents the (—CH=CH—) group, (e) where appropriate hydrogenation of a resulting compound of the general formula I in which A-B represents a (—CH=CH—) group to give a compound of the general formula I in which A-B represents a (—CH$_2$—CH$_2$—) group, it also being possible for the hydrogenation to be carried out on the compounds of the formula V, VI or VII to give compounds in which A-B represents the (—CH$_2$—CH$_2$—) group, (f) where appropriate conversion of a hydroxylactone of the general formula I into the corresponding dihydroxy acid of the formula II, or its salts, or, where appropriate, preparation from the hydroxylactone I or the free hydroxy acid II of the corresponding esters.

The phosphonium salts which are used as starting material in the process according to the invention and have the general formula III, in which $R^1$, $R^2$ and $R^3$ have the meaning given for the general formula I, are obtained as depicted in scheme 1.

Ketones of the general formula VIII, where $R^2$ and $R^3$ have the indicated meaning, are known from the literature or can be prepared by processes known from the literature (cf., for example, D. Vorländer and F. Kalkow, Berichte d. Dtsch. Chem. Ges. 30, 2268 (1897) or H. Stetter in Houben-Weyl, Methoden der Organischen Chemie (Methods of Organic Chemistry) Vol. VII/26, 1449–1507, Thieme, Stuttgart 1976). Likewise known from the literature or amenable to preparation by processes known from the literature (for example in analogy to M. Jackman, M. Klenk, B. Fishburn, B. F. Tullar and S. Archer, J. Am. Chem. Soc. 70, 2884 (1948)) are the β-keto esters of the general formula IX, where $R^1$ has the abovementioned meaning, and $R^{10}$ denotes a straight-chain or branched alkyl radical having up to 6 carbon atoms, preferably a methyl or ethyl radical.

Compounds of the formula X in which $R^1$, $R^2$, $R^3$ and $R^{10}$ have the indicated meaning are prepared in analogy to literature processes, for example according to R. Connor, D. B. Andrews, J. Am. Chem. Soc. 56 2713 (1943) and literature cited therein. An example of a process used to convert compounds of the type X into pyridines of the general formula XV (in this, $R^1$, $R^2$ and $R^3$ have the abovementioned meaning, and Z denotes a CH group) is that described by F. Rehberg and F. Kröhnke, Liebigs Ann. Chem. 717, 91 (1968).

Dihydropyrimidines of the general formula XIV can be prepared, for example, in analogy to a literature process (E. F. Silversmith, J. Org. Chem. 27, 4090 (1962)) or, for example, also by a synthesis shown in scheme 1, route A, by reacting a β-keto ester of the general formula IX with an aldehyde of the type XI to give a compound of the general formula XII, and reacting the latter, without further purification, with an amidinium compound of the type XIII to give a dihydropyrimidinecarboxylic ester of the general formula XIV. The preparation of compounds of the type XIV from components of the general formulae IX, XI and XIII can likewise be carried out as a one-pot reaction (scheme 1, route B).

The oxidation of compounds of the formula XIV to give pyrimidinecarboxylic esters of the general formula XV in which $R^1$, $R^2$, $R^3$ and $R^{10}$ have the abovementioned meaning, and Z denotes a nitrogen atom, is carried out in analogy to processes known from the literature, for example by dehydrogenation using chloroanil or 2,3-dichloro-5,6-dicyano-p-benzoquinone (DDQ) as described by E. A. Braude, J. Hannah, R. Linstead, J. Chem. Soc. 1960, 3257.

Compounds of the general formula XV are reduced by reaction with complex metal hydrides such as, for example, lithium aluminum hydride or diisobutylaluminum hydride, in aprotic solvents, for example diethyl ether or tetrahydrofuran, at temperatures between $-30°$ C. and $+50°$ C.

Alkyl halides of the general formula XVII, where $R^1$, $R^2$, $R^3$ and X have the abovementioned meaning, can be prepared from alcohols of the type XVI, for example by reaction with phosphorus halides in inert solvents such as, for example, dichloromethane or toluene, at temperatures between $0°$ and $100°$ C., or by reaction with hydrohalic acids.

Phosphonium salts of the general formula III are obtained by, for example, reaction of the alkyl halides XVII with triphenylphosphine in inert solvents such as toluene, at temperatures between $20°$ C. and $120°$ C. (cf. scheme 1).

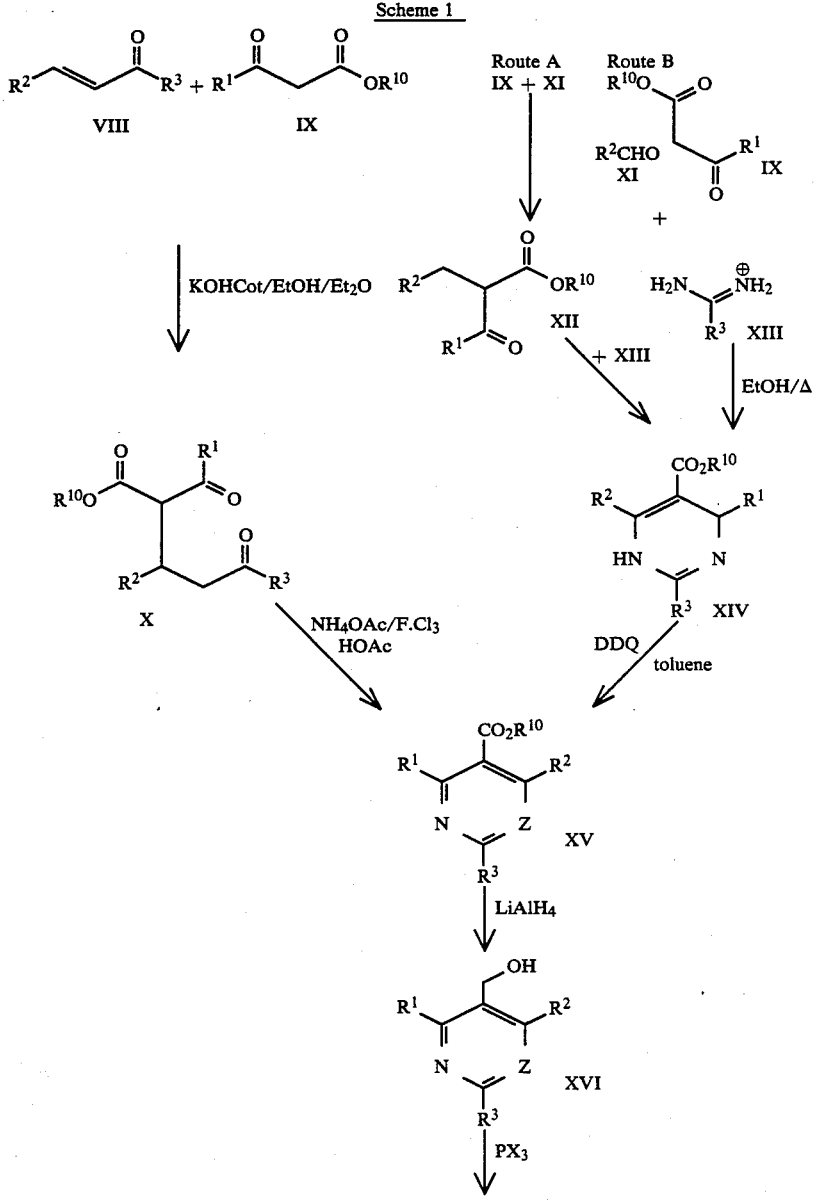

Scheme 1 -continued

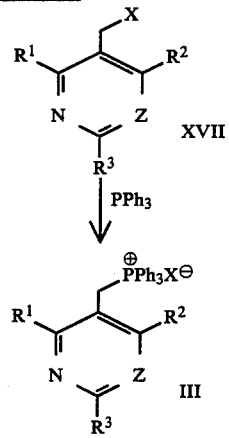

The chiral aldehyde of the formula IV which is used as starting material in the process according to the invention is obtained by a process known from the literature (Yuh Lin, J. R. Falck, Tetrahedron Letters 23, 4305–4308 (1982)) from the corresponding alcohol by oxidation with, for example, $CrO_3$ or oxalyl chloride/-dimethyl sulfoxide in the presence of triethylamine.

Reaction of the chiral aldehyde of the formula IV with a phosphonium salt of the formula III by the Wittig method (for example Wittig, Haag, Chem. Ber. 88, 1654 (1955)) results in compounds of the formula V, a preferred embodiment comprising dissolution or suspension of phosphonium salts of the formula III in a solvent such as tetrahydrofuran, dimethyl sulfoxide or DME, liberation of the corresponding phosphoranes using a suitable strong base such as, for example, sodium hydride, potassium tert.-butylate, Li ethylate or butyllithium, and then addition of the aldehyde of the formula IV and allowing reaction to take place at $-10°$ C. to $+50°$ C. for 1–6 h.

In this, the compounds of the formula V are mainly obtained in the form of mixtures of the E/Z olefins. Mixtures of E/Z olefins can, where appropriate, be fractionated by chromatography. The pure Z-olefins can also be obtained, as described by G. Drefahl Chem. Ber. 94, 907 (1961), by irradiation of the E/Z mixture in solutions, such as, for example, toluene or nitrobenzene.

The corresponding pure E-olefins can be obtained, as described by De Tar et al. in J. Amer. Chem. Soc. 78, 474 (1955), by heating the E/Z mixtures in solution in the presence of iodine.

The methyl acetal protective group in the compounds of the formula V can be selectively eliminated by acid hydrolysis in the generally customary manner, preferably using a mixture of glacial acetic acid, tetrahydrofuran and water in the ratio 3:2:2, at $+20°$ to $+90°$ C., within 6–24 hours.

Oxidation of the compounds of the formula VI to give a lactone of the formula VII can be carried out by oxidizing agents such as $CrO_3 \times 2Pyr$, or pyridinium chlorochromate in inert solvents such as, for example, methylene chloride or chloroform. Further possibilities for the oxidation comprise reaction with thioanisole/$Cl_2$/$NEt_3$ in carbon tetrachloride, reaction with DMSO/oxalyl chloride/$NEt_3$ at $-20°$ C., or reaction with N-iodosuccinimide/tetrabutylammonium iodide in dichloromethane.

To prepare the compounds of the formula I, the protective group $R^9$ in the compounds of the formula VII is eliminated. This can take place with strong acids, such as 5-normal hydrochloric acid or sulfuric acid, at $-10°$ C. to $+30°$ C., or with fluoride ions, preferably by dissolving the compounds of the formula VII in tetrahydrofuran or diethyl ether, and adding a mixture of tetrabutylammonium fluoride and glacial acetic acid, followed by stirring at $0°$ C. to $40°$ C. for between 1 and 12 hours.

Compounds of the formula I in which A-B represents a (CH=CH) group are hydrogenated by a generally customary method, expediently at a temperature between $20°$ C. and $40°$ C. using hydrogen in the presence of a metal catalyst, preferably palladium, platinum, $PtO_2$ or $PdO_2$, to give compounds of the formula I, in which A-B denotes a $-CH_2-CH_2-$ group. This hydrogenation can be carried out under atmospheric pressure in customary solvents such as tetrahydrofuran, ethyl acetate, methanol, low molecular weight alcohols, glacial acetic acid or chloroform, or in autoclaves under elevated pressure (2–50 atm). The hydrogenation of the $-CH=CH-$ group can also be carried out on the compounds of the formulae V, VI or VII.

The resulting compounds of the formula I can be isolated in a straightforward manner by evaporation of the solvent, where appropriate after purification by chromatography.

The compounds of the formula I are obtained in optically pure form. Concerning the configuration of the double bond (A-B=$-$CH=CH$-$), E/Z mixtures are obtained, and these can, at all stages of the synthesis, be fractionated by chromatography or isomerized to give the E form (cf. in this context, De Tar et al., J. Amer. Chem. Soc. 78 475 (1955)).

Compounds of the formula I in the form of the δ-lactone can be hydrolyzed in alkaline medium to give the corresponding salts of the dihydroxy acids, for example using NaOH or KOH in a low molecular weight alcohol such as methanol, or in ethers such as dimethoxyethane or THF, where appropriate in the presence of water. The alkali metal cation in the resulting salts of the dihydroxy acids can, after acidification, be exchanged by any desired cations in ion exchangers in the customary manner. For this purpose, for example, the dihydroxy acids are allowed to run through a column packed with a cation exchanger, such as, for example, based on polystyrene/divinylbenzene (®AMBERLITE CG-150 or ®DOWEX CCR-2). The cation exchanger is loaded with the desired cation, for example with ammonium ions derived from a primary, secondary or tertiary amine. The desired salt is obtained by evaporation of the eluate.

Ammonium salts of the dihydroxy acids, which are derived from a primary, secondary or tertiary amine, can also be prepared by mixing the free dihydroxy acids in an alcohol solution with an equimolar amount of the appropriate amine, and evaporating the solvent.

The free dihydroxy acids II of the δ-lactones I can be esterified by customary methods, for example using a diazoalkane. Thus, for example, compounds of the formula I can be esterified with a diazoalkane at temperatures between $-40°$ C. and $+20°$ C., it being possible to use the customary solvents such as, for example, diethyl ether, tetrahydrofuran, chloroform or low molecular weight alcohols such as methanol. The resulting esters can be isolated in a straightforward manner by evaporation of the solvent and, where appropriate, purified by chromatography. Another esterification method comprises reaction of salts of the dihydroxy acids II with an alkylating agent in the presence of a base such as, for example, a metal alcoholate or metal carbonate in a suitable solvent. An example of a suitable metal alcoholate is sodium ethylate or potassium tertiarybutylate. Suitable solvents are alcohols such as, for example, methanol or tert.-butanol, ethers such as tetrahydrofuran or 1,2-dimethoxyethane and, in particular, dipolar aprotic solvents such as dimethylformamide, dimethylsulfoxide, acetonitrile or N-methylpyrrolidone. Another suitable method for the preparation of esters of the dihydroxy acids is transesterification with an excess of alcohols, such as, for example, methanol, ethanol or isopropanol.

Where the individual reaction products do not result in a form which is sufficiently pure for them to be used in the subsequent reaction step, it is advisable to purify by crystallization, or column, thin-layer or high-pressure liquid chromatography.

If the aldehyde of the formula IV is not in the form of the pure enantiomer, it is also possible for mixtures of the enantiomeric final products to be produced, and these can be fractionated by generally customary processes.

It is expedient in the synthesis of compounds of the general formulae I and II in which $R^1$, $R^2$ and $R^3$, independently of one another, contain hydroxyl groups to use starting compounds of the general formulae VIII-XII in which the hydroxyl groups are protected in a suitable manner, for example as alkyl or silyl ethers. The compounds then obtained in the process according to the invention are of the general formulae I or II in which $R^1$, $R^2$ or $R^3$ contain the correspondingly protected hydroxyl groups. The latter can be converted, by elimination of the protective groups by processes known from the literature, into compounds of the general formula I with hydroxyl-substituted radicals $R^1$, $R^2$ or $R^3$. Suitable protective groups, as well as methods for the introduction and removal thereof, are known from the literature (cf. for example T. W. Greene, Protective Groups in Organic Synthesis, Wiley and Sons, N.Y., 1981).

In more cases, where the intention is to prepare compounds of the general formulae I and II with acid-sensitive radicals $R^1$, $R^2$ or $R^3$, this can also take place by the process described in patent application No. P37 22 807.2.

Apart from the compounds described in the examples, the process according to the invention can be used to prepare the following compounds:

E-6S-(2-(2-Cyclohexyl-4-(4-fluorophenyl)-6-phenylpyridin-3-yl)ethenyl)-4R-hydroxy-3,4,5,6-tetrahydro-2H-pyran-2-one E-6S-(2-(4-Cyclohexyl-2-(4-fluorophenyl)-6-phenylpyridin-3-yl)ethenyl)-4R-hydroxy-3,4,5,6-tetrahydro-2H-pyran-2-one E-6S-(2-(4-Cyclohexylmethyl)-2-(1-methylethyl)-6-phenylpyridin-3-yl)ethenyl)-4R-hydroxy-3,4,5,6-tetrahydro-2H-pyran-2-one E-6S-(2-(2-Cyclohexylmethyl)-2-(1-methylethyl)-6-phenylpyridin-3-yl)ethenyl)-4R-hydroxy-3,4,5,6-tetrahydro-2H-pyran-2-one E-6S-(2-(4-(3,5-Dimethylphenyl)-2-(1-methylethyl-6-phenylpyridin-3-yl)ethenyl)-4R-hydroxy-3,4,5,6-tetrahydro-2H-pyran-2-one E-6S-(2-(2-(3,5-Dimethylphenyl)-2-(1-methylethyl-6-phenylpyridin-3-yl)ethenyl)-4R-hydroxy-3,4,5,6-tetrahydro-2H-pyran-2-one E-6S-(2-(4,6-Diphenyl-2-(1-methylethyl)pyridin-3-yl)ethenyl)-4R-hydroxy-3,4,5,6-tetrahydro-2H-pyran-2-one E-6S-(2-(2,6-Diphenyl-2-(1-methylethyl)pyridin-3-yl)ethenyl)-4R-hydroxy-3,4,5,6-tetrahydro-2H-pyran-2-one E-6S-(2-(2-(1-Methylethyl)-6-phenyl-4-(4-trifluoromethylphenyl)pyridin-3-yl)ethenyl)-4R-hydroxy-3,4,5,6-tetrahydro-2H-pyran-2-one E-6S-(2-(4-(1-Methylethyl)-6-phenyl-4-(4-trifluoromethylphenyl)pyridin-3-yl)ethenyl)-4R-hydroxy-3,4,5,6-tetrahydro-2H-pyran-2-one E-6S-(2-(4-(4-Fluoro-3-methylphenyl)-2-(1-methylethyl)-6-phenylpyridin-3-yl)ethenyl)-4R-hydroxy-3,4,5,6-tetrahydro-2H-pyran-2-one E-6S-(2-(2-(4-Fluoro-3-methylphenyl)-2-(1-methylethyl)-6-phenylpyridin-3-yl)ethenyl)-4R-hydroxy-3,4,5,6-tetrahydro-2H-pyran-2-one E-6S-(2-(6-(4-Fluorophenyl)-2-(1-methylethyl)-4-phenylpyridin-3-yl)ethenyl)-4R-hydroxy-3,4,5,6-tetrahydro-2H-pyran-2-one E-6S-(2-(6-(4-Fluorophenyl)-4-(1-methylethyl)-2-phenylpyridin-3-yl)ethenyl)-4R-hydroxy-3,4,5,6-tetrahydro-2H-pyran-2-one E-6S-(2-(6-(3,5-Dimethylphenyl)-4-(4-fluorophenyl)-2-(1-methylethyl)pyridin-3-yl)ethenyl)-4R-hydroxy-3,4,5,6-tetrahydro-2H-pyran-2-one E-6S-(2-(6-(3,5-Dimethylphenyl)-2-(4-fluorophenyl)-4-(1-methylethyl)pyridin-3-yl)ethenyl)-4R-hydroxy-3,4,5,6-tetrahydro-2H-pyran-2-one E-6S-(2-(4,6-Bis-(1-methylethyl)-2-(4-fluorophenyl)-pyridin-3-yl)ethenyl)-4R-hydroxy-3,4,5,6-tetrahydro-2H-pyran-2-one E-6S-(2-(2,6-Bis-(1-methylethyl)-4-(4-fluorophenyl)-pyridin-3-yl)ethenyl)-4R-hydroxy-3,4,5,6-tetrahydro-2H-pyran-2-one E-6S-(2-(4-(4-Fluorophenyl)-2-(1-methylethyl)-6-(4-trifluoromethylphenyl)pyridin-3-yl)ethenyl)-4R-hydroxy-3,4,5,6-tetrahydro-2H-pyran-2-one E-6S-(2-(2-(4-Fluorophenyl)-4-(1-methylethyl)-6-(4-trifluoromethylphenyl)pyridin-3-yl)ethenyl)-4R-hydroxy-3,4,5,6-tetrahydro-2H-pyran-2-one E-6S-(2-(6-(4-Fluorophenyl)-4-(4-methoxyphenyl)-2-(1-methylethyl)pyridin-3-yl)ethenyl)-4R-hydroxy-3,4,5,6-tetrahydro-2H-pyran-2-one E-6S-(2-(6-(4-Fluorophenyl)-2-(4-methoxyphenyl)-2-(1-methylethyl)pyridin-3-yl)ethenyl)-4R-hydroxy-3,4,5,6-tetrahydro-2H-pyran-2-one E-6S-(2-(2,6-Bis(1,1-dimethylethyl)-4-(4-fluorophenyl)-pyridin-3-yl)ethenyl)-4R-hydroxy-3,4,5,6-tetrahydro-2H-pyran-2-one E-6S-(2-(4,6-Bis(1,1-dimethylethyl)-2-(4-fluorophenyl)-pyridin-3-yl)ethenyl)-4R-hydroxy-3,4,5,6-tetrahydro-2H-pyran-2-one E-6S-(2-(4,6-Dimethyl-2-(4-fluorophenyl)pyridin-3-yl)ethenyl)-4R-hydroxy-3,4,5,6-tetrahydro-2H-pyran-2-one E-6S-(2-(2-Chlorophenyl)-4,6-dimethylpyridin-3-yl)-ethenyl)-4R-hydroxy-3,4,5,6-tetrahydro-2H-pyran-2-one E-6S-(2-(2-(4-Fluorophenyl)-4-methyl-6-phenylpyridin-3-yl)ethenyl)-4R-hydroxy-3,4,5,6-tetrahydro-2H-pyran-2-one E-6S-(2-(2-(4-Fluorophenyl)-6-methyl-4-(1-methylethyl)pyridin-3-yl)ethenyl)-4R-hydroxy-3,4,5,6-tetrahydro-2H-pyran-2-one E-6S-(2-(4-(1,1-Dimethylethyl)-2-(4-fluorophenyl)-6-phenylpyridin-3-yl)ethenyl)-4R-hydroxy-3,4,5,6-tetrahydro-2H-pyran-2-one E-6S-(2-(2,6-Dimethyl-4-(4-methoxyphenyl)pyridin-3-yl)ethenyl)-4R-hydroxy-3,4,5,6-tetrahydro-2H-pyran-2-one E-6S-(2-(4,6-Dimethyl-2-(4-methoxyphenyl)pyridin-3-yl)ethenyl)-4R-hydroxy-3,4,5,6-tetrahydro-2H-pyran-2-one E-6S-(2-(4-(4-Methoxyphenyl)-6-methyl-2-(1-methylethyl)pyridin-3-yl)ethenyl)-4R-hydroxy-3,4,5,6-tetrahydro-2H-pyran-2-one E-6S-(2-(2-(4-Methoxyphenyl)-6-methyl-4-(1-methylethyl)pyridin-3-yl)ethenyl)-4R-hydroxy-3,4,5,6-tetrahydro-2H-pyran-2-one E-6S-(2-(2-(4-Methoxyphenyl)-4-(1-methylethyl)-6-phenylpyridin-3-yl)ethenyl)-4R-hydroxy-3,4,5,6-tetrahydro-2H-pyran-2-one E-6S-(2-(6-(2,5-Dimethylphenyl)-2-(4-fluorophenyl)-4-(1-methylethyl)pyridin-3-yl)ethenyl)-4R-hydroxy-3,4,5,6-tetrahydro-2H-pyran-2-one E-6S-(2-(2,4-Bis-(4-fluorophenyl)-4-(1-methylethyl)-pyridin-3-yl)ethenyl)-4R-hydroxy-3,4,5,6-tetrahydro-2H-pyran-2-one E-6S-(2-(6-Cyclohexyl-4-(4-fluorophenyl)-2-(1-methylethyl)pyridin-3-yl)ethenyl)-4R-hydroxy-3,4,5,6-tetrahydro-2H-pyran-2-one E-6S-(2-(6-Cyclohexyl-2-(4-fluorophenyl)-4-(1-methylethyl)pyridin-3-yl)ethenyl)-4R-hydroxy-3,4,5,6-tetrahydro-2H-pyran-2-one E-6S-(2-(4-(4-Fluorophenyl)-2-(1R-methylpropyl)-6-phenylpyridin-3-yl)ethenyl)-4R-hydroxy-3,4,5,6-tetrahydro-2H-pyran-2-one E-6S-(2-(4-(4-Fluorophenyl)-2-(1S-methylpropyl)-6-phenylpyridin-3-yl)ethenyl)-4R-hydroxy-3,4,5,6-tetrahydro-2H-pyran-2-one E-6S-(2-(2-(4-Fluorophenyl)-4-(1R-methylpropyl)-6-phenylpyridin-3-yl)ethenyl)-4R-hydroxy-3,4,5,6-tetrahydro-2H-pyran-2-one E-6S-(2-(2-(4-Fluorophenyl)-4-(1S-methylpropyl)-6-phenylpyridin-3-yl)ethenyl)-4R-hydroxy-3,4,5,6-tetrahydro-2H-pyran-2-one E-6S-(2-(2,6-Dimethyl-4-(4-fluorophenyl)pyridin-3-yl)ethyl)-4R-hydroxy-3,4,5,6-tetrahydro-2H-pyran-2-one E-6S-(2-(4-(4-Fluorophenyl)-2-(1-methylethyl)-6-phenylpyridin-3-yl)ethyl)-4R-hydroxy-3,4,5,6-tetrahydro-2H-pyran-2-one E-6S-(2-(2-(4-Fluorophenyl)-4-(1-methylethyl)-6-phenylpyridin-3-yl)ethyl)-4R-hydroxy-3,4,5,6-tetrahydro-2H-pyran-2-one E-6S-(2-(2-Cyclohexyl-4-(4-fluorophenyl)-6-phenylpyridin-3-yl)ethyl)-4R-hydroxy-3,4,5,6-tetrahydro-2H-pyran-2-one E-6S-(2-(4-(4-Methoxyphenyl)-2-(1-methylethyl)-6-phenyl)ethyl)-4R-hydroxy-3,4,5,6-tetrahydro-2H-pyran-2-one E-6S-(2-(6-(2,5-Dimethylphenyl)-4-(4-fluorophenyl)-2-(1-methylethyl)pyridin-3-yl)ethyl)-4R-hydroxy-3,4,5,6-tetrahydro-2H-pyran-2-one E-6S-(2-(6-(3,5-Dimethylphenyl)-4-(4-fluorophenyl)-2-(1-methylethyl)pyridin-3-yl)ethyl)-4R-hydroxy-3,4,5,6-tetrahydro-2H-pyran-2-one E-6S-(2-(5-(2-Phenyl-4-(4-fluorophenyl)-6-isopropyl)-pyrimidinyl)ethenyl)-4R-hydroxy-3,4,5,6-tetrahydro-2H-pyran-2-one E-6S-(2-(5-(2-(2-Methylphenyl)-4-(4-chlorophenyl)-6-isopropyl)pyrimidinyl)ethenyl)-4R-hydroxy-3,4,5,6-tetrahydro-2H-pyran-2-one E-6S-(2-(5-(2-(2,6-Dimethylphenyl)-4-(4-fluorophenyl)-6-isopropyl)pyrimidinyl)ethenyl)-4R-hydroxy-3,4,5,6-tetrahydro-2H-pyran-2-one E-6S-(2-(5-(2-(2,6-Dichlorophenyl)-4-(4-fluorophenyl)-6-isopropyl)pyrimidinyl)ethenyl)-4R-hydroxy-3,4,5,6-tetrahydro-2H-pyran-2-one E-6S-(2-(5-(2-Phenyl-4-(4-chlorophenyl)-6-t-butyl)-pyrimidinyl)ethenyl)-4R-hydroxy-3,4,5,6-tetrahydro-2H-pyran-2-one E-6S-(2-(5-(2-Phenyl-4-(4-fluorophenyl)-6-t-butyl)-pyrimidinyl)ethyl)-4R-hydroxy-3,4,5,6-tetrahydro-2H-pyran-2-one E-6S-(2-(5-(2-Phenyl-4-(4-fluoro-3-methylphenyl)-6-isopropylpyrimidinyl)ethenyl)-4R-hydroxy-3,4,5,6-tetrahydro-2H-pyran-2-one E-6S-(2-(5-(2-Phenyl-4-(4-fluoro-3-methylphenyl)-6-isopropylpyrimidinyl)ethyl)-4R-hydroxy-3,4,5,6-tetrahydro-2H-pyran-2-one E-6S-(2-(5-(2,6-Diisopropyl-4-(4-chlorophenyl)-pyrimidinyl)ethenyl)-4R-hydroxy-3,4,5,6-tetrahydro-2H-pyran-2-one E-6S-(2-(5-(2,6-Diisopropyl-4-(4-methoxyphenyl)-pyrimidinyl)ethenyl)-4R-hydroxy-3,4,5,6-tetrahydro-2H-pyran-2-one E-6S-(2-(5-(2,6-Dimethyl-4-cyclohexylpyrimidinyl)ethenyl)-4R-hydroxy-3,4,5,6-tetrahydro-2H-pyran-2-one E-6S-(2-(5-(2,6-Diisopropyl-4-cyclohexyl)pyrimidinyl)ethenyl)-4R-hydroxy-3,4,5,6-tetrahydro-2H-pyran-2-one E-6S-(2-(5-(2-Phenyl-4-cyclohexyl-6-isopropyl)-pyrimidinyl)ethenyl)-4R-hydroxy-3,4,5,6-tetrahydro-2H-pyran-2-one E-6S-(2-(5-(2,6-Ditert.-butyl-4-(4-chlorophenyl)-pyrimidinyl)ethenyl)-4R-hydroxy-3,4,5,6-tetrahydro-2H-pyran-2-one E-6S-(2-(5-(2,6-Ditert.-butyl-4-(4-fluorophenyl)-pyrimidinyl)ethenyl)-4R-hydroxy-3,4,5,6-tetrahydro-2H-pyran-2-one E-6S-(2-(5-(2-Methyl-4(4-fluoro-3-methylphenyl)-6-isopropyl)pyrimidinyl)ethenyl)-4R-hydroxy-3,4,5,6-tetrahydro-2H-pyran-2-one E-6S-(2-(5-(2-Methyl-4(4-fluorophenyl)-6-isopropyl)-
  pyrimidinyl)ethyl)-4R-hydroxy-3,4,5,6-tetrahydro-
  2H-pyran-2-one
E-6S-(2-(5-(2-(2,6-Dichlorophenyl)-4-(4-fluorophenyl)-
  6-isopropyl)pyrimidinyl)ethenyl)-4R-hydroxy-
  3,4,5,6-tetrahydro-2H-pyran-2-one
E-6S-(2-(5-(2-(2-Chloro-4-methylphenyl)-4-(4-chloro-
  phenyl)-6-isopropyl)pyrimidinyl)ethenyl)-4R-
  hydroxy-3,4,5,6-tetrahydro-2H-pyran-2-one
E-6S-(2-(5-(2-(2,4-Dichlorophenyl)-4-(4-fluorophenyl)-
  6-methyl)pyrimidinyl)ethenyl)-4R-hydroxy-3,4,5,6-
  tetrahydro-2H-pyran-2-one
E-6S-(2-(5-(2-(2,4-Dimethyl-phenyl)-4-(4-methoxy-
  phenyl)-6-isopropyl)pyrimidinyl)ethyl)-4R-hydroxy-
  3,4,5,6-tetrahydro-2H-pyran-2-one
E-6S-(2-(5-(2-(2-Chloro-4-methyl-phenyl)-4-(4-fluoro-
  3-phenyl)-6-isopropyl)pyrimidinyl)ethenyl)-4R-
  hydroxy-3,4,5,6-tetrahydro-2H-pyran-2-one
E-6S-(2-(5-(2-Methyl-4-phenyl-6-tert.butyl)-
  pyrimidinyl)ethenyl)-4R-hydroxy-3,4,5,6-tetrahydro-
  2H-pyran-2-one
E-6S-(2-(5-(2-Methyl-4-phenyl-6-tert.butyl)-
  pyrimidinyl)ethyl)-4R-hydroxy-3,4,5,6-tetrahydro-
  2H-pyran-2-one
E-6S-(2-(5-(2-Phenyl-4-(4-fluorophenyl)-6-isopropyl)-
  pyrimidinyl)ethenyl)-4R-hydroxy-3,4,5,6-tetrahydro-
  2H-pyran-2-one
E-6S-(2-(5-(2-Phenyl-4-(4-fluoro-3-methyl-phenyl)-6-
  tert.butyl)pyrimidinyl)ethenyl)-4R-hydroxy-3,4,5,6-tet-
  rahydro-2H-pyran-2-one
E-6S-(2-(2-(4-Fluorophenyl)-6-(4-hydroxyphenyl)-4-(1-
  methylethyl)pyridin-3-yl)ethenyl)-4R-hydroxy-
  3,4,5,6-tetrahydro-2H-pyran-2-one
E-6S-(2-(2-(4-Hydroxyphenyl)-4-(1-methylethyl)-6-
  phenylpyridin-3-yl)ethenyl)-4R-hydroxy-3,4,5,6-tet-
  rahydro-2H-pyran-2-one
E-6S-(2-(4-Cyclopropyl-2-(4-fluorphenyl)-6-phenyl-
  pyridin-3-yl)ethenyl)-4R-hydroxy-3,4,5,6-tetrahydro-
  2H-pyran-2-one

BIOLOGICAL ASSAY SYSTEMS

1. HMG-CoA reductase activity in enzyme preparations

The HMG-CoA reductase activity was measured on solubilized enzyme preparations from rat liver microsomes induced, after a changeover in the day/night rhythm, with cholestyramine (® CUEMID). The substrate used was (S,R)-$^{14}$C-HMG-CoA, and the NADPH concentration was maintained during the incubation by a regenerating system. $^{14}$C-Mevalonate was separated from the substrate and other products (for example $^{14}$C-HMG) by column elution, the elution profile of each individual sample being determined. $^3$H-Mevalonate was not always included in the determination because relative data on the inhibitory effects were required. In each series of tests, the enzyme-free control, the enzyme-containing normal mixture (=100%) and those with additions of product, final concentration $10^{-5}$ to $10^{-9}$ M, were treated together. Each individual value was the mean formed from 3 parallel samples. The significance of the mean differences between product-free and product-containing samples was assessed using the t test.

Using the method described above, the following values for the inhibition of HMG-CoA reductase was determined for the compounds according to the invention, for example [IC$_{50}$/mol/liter denotes the molar concentration of the compound required for 50% inhibition]:

TABLE 1

| Compound of Example | Z | R$^1$ | R$^2$ | R$^3$ | A-B | IC$_{50}$/mol/Liter |
|---|---|---|---|---|---|---|
| 13a | CH | CH$_3$ | 4-FC$_6$H$_4$ | CH$_3$ | (E)—CH≡CH | $2.6 \cdot 10^{-7}$ |
| 13b | CH | CH$_3$ | 4-ClC$_6$H$_4$ | CH$_3$ | (E)—CH≡CH | $9.4 \cdot 10^{-8}$ |
| 13c | CH | CH$_3$ | 4-FC$_6$H$_4$ | C$_6$H$_5$ | (E)—CH≡CH | $3.8 \cdot 10^{-8}$ |
| 13d | CH | iC$_3$H$_7$ | 4-FC$_6$H$_4$ | CH$_3$ | (E)—CH≡CH | $9.1 \cdot 10^{-9}$ |
| 13e | CH | iC$_3$H$_7$ | 4-FC$_6$H$_4$ | C$_6$H$_5$ | (E)—CH≡CH | $2.9 \cdot 10^{-9}$ |
| 13f | CH | 4-FC$_6$H$_4$ | iC$_3$H$_7$ | C$_6$H$_5$ | (E)—CH≡CH | $4.0 \cdot 10^{-9}$ |
| 13g | CH | tC$_4$H$_9$ | 4-FC$_6$H$_4$ | C$_6$H$_5$ | (E)—CH≡CH | $1.8 \cdot 10^{-8}$ |
| 13i | CH | iC$_3$H$_7$ | 4-FC$_6$H$_4$ | 2.5-(CH$_3$)$_2$C$_6$H$_4$ | (E)—CH≡CH | $5.0 \cdot 10^{-9}$ |
| 13j | CH | iC$_3$H$_7$ | 4-FC$_6$H$_4$ | 4-FC$_6$H$_4$ | (E)—CH≡CH | $2.3 \cdot 10^{-9}$ |
| 13k | N | CH$_3$ | 4-FC$_6$H$_4$ | CH$_3$ | (E)—CH≡CH | $5.0 \cdot 10^{-7}$ |
| 13l | N | CH$_3$ | 4-ClC$_6$H$_4$ | CH$_3$ | (E)—CH≡CH | $6.0 \cdot 10^{-7}$ |
| 13o | N | iC$_3$H$_7$ | 4-FC$_6$H$_4$ | C$_6$H$_5$ | (E)—CH≡CH | $3.0 \cdot 10^{-9}$ |
| 13q | CH | iC$_3$H$_7$ | 4-FC$_6$H$_4$ | iC$_3$H$_7$ | (E)—CH≡CH | $2.5 \cdot 10^{-9}$ |
| 13r | CH | 1C$_3$H$_7$ | 4-FC$_6$H$_4$ | tC$_4$H$_9$ | (E)—CH≡CH | $1.2 \cdot 10^{-9}$ |
| 13s | CH | iC$_3$H$_7$ | 4-FC$_6$H$_4$ | cC$_6$H$_{11}$ | (E)—CH≡CH | $3.7 \cdot 10^{-9}$ |
| missing | | | | | | |
| missing | | | | | | |
| 13v | N | iC$_3$H$_7$ | 4-FC$_6$H$_4$ | iC$_3$H$_7$ | (E)—CH≡CH | $2.5 \cdot 10^{-9}$ |
| 13w | N | iC$_3$H$_7$ | 4-FC$_6$H$_4$ | 4-FC$_6$H$_4$ | (E)—CH≡CH | $0.9 \cdot 10^{-9}$ |
| 13z | N | iC$_3$H$_7$ | 4-FC$_6$H$_4$ | C$_6$H$_5$ | —CH$_2$—$_{CH2}$— | $3.3 \cdot 10^{-9}$ |
| 13ab | CH | iC$_3$H$_7$ | 4-FC$_6$H$_4$ | 4-HOC$_6$H$_4$ | (E)—CH≡CH | $1.5 \cdot 10^{-9}$ |
| 13ac | CH | cC$_3$H$_5$ | 4-FC$_6$H$_4$ | C$_6$H$_5$ | (E)—CH≡CH | $1.0 \cdot 10^{-9}$ |

2. Suppression or inhibition of HMG-CoA reductase in cell cultures of HEP-G2 cells Monolayers of HEP-G2 cells in lipoprotein-free nutrient medium were preincubated with appropriate concentrations of the test substances for a defined time (for example 1 hour), the labeled precursor, for example sodium $^{14}$C-acetate was added and then the incubation was continued (for example for 3 hours). Addition of an internal standard ($^3$H-cholesterol) was followed by alkaline hydrolysis of some of the cells. The lipids were extracted from the hydrolyzed cells using chloroform/methanol. Carrier cholesterol was added to this lipid mixture which was then subjected to preparative thin-layer chromatography, the cholesterol band was visualized with iodine vapor and then isolated, and the amount of $^{14}$C-cholesterol formed from the $^{14}$C-precursor was determined by scintigraphy. Cellular protein was determined in an aliquot of the cells, so that it is possible to calculate the amount of $^{14}$C-cholesterol formed per mg of cellular protein in unit time. Comparison of this figure with the amount of $^{14}$C-cholesterol formed per mg of cellular protein and unit time in a culture treated in the same way but containing no test substance revealed the inhibitory effect of the particular test product on the cholesterol biosynthesis of HEP-G2 cell cultures.

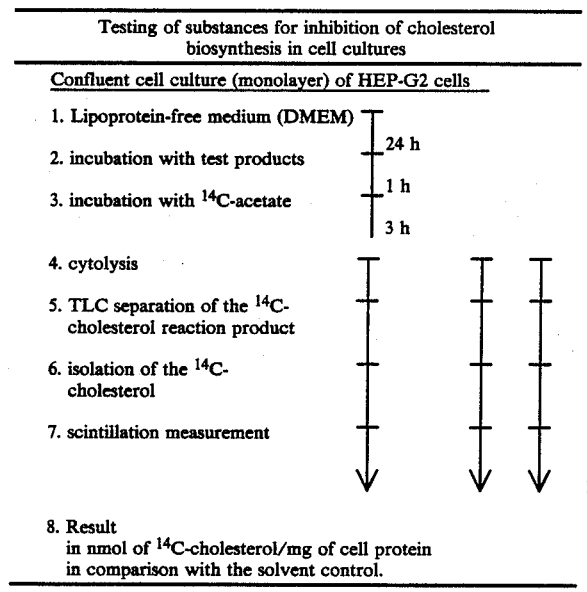

Testing of substances for inhibition of cholesterol biosynthesis in cell cultures Confluent cell culture (monolayer) of HEP-G2 cells 1. Lipoprotein-free medium (DMEM)    24 h
2. incubation with test products
3. incubation with $^{14}$C-acetate    1 h
   3 h
4. cytolysis
5. TLC separation of the $^{14}$C-cholesterol reaction product
6. isolation of the $^{14}$C-cholesterol
7. scintillation measurement
8. Result
   in nmol of $^{14}$C-cholesterol/mg of cell protein in comparison with the solvent control.

Using the method described above, the following values for the inhibition of cholesterol biosynthesis (in HEP-G2 cells) were determined for the compounds according to the invention, for example (the IC$_{50}$/mol/-liter is the concentration of the compound which brings about 50% inhibition of cholesterol biosynthesis) (Tab. 2):

TABLE 2

| Compound of Example | Z | R$^1$ | R$^2$ | R$^3$ | A-B | IC$_{50}$/mol/ liter |
|---|---|---|---|---|---|---|
| 11c | CH | CH$_3$ | 4-F-C$_6$H$_4$ | C$_6$H$_5$ | (E)—CH≡CH | $9 \cdot 10^{-8}$ |
| 11d | CH | i-C$_3$H$_7$ | 4-F-C$_6$H$_4$ | CH$_3$ | (E)—CH≡CH | $5 \cdot 10^{-8}$ |
| 11e | CH | i-C$_3$H$_7$ | 4-F-C$_6$H$_4$ | C$_6$H$_5$ | (E)—CH≡CH | $5 \cdot 10^{-9}$ |
| 11o | N | i-C$_3$H$_7$ | 4-F-C$_6$H$_4$ | C$_6$H$_5$ | (E)—CH≡CH | $5 \cdot 10^{-9}$ |

The compounds of the general formula I or II are distinguished by strong inhibition of HMG-CoA reductase, the rate-determining enzyme of cholesterol biosynthesis.

The extent of inhibition which is characterized by IC$_{50}$ values in the range $10^{-7}$–$10^{-9}$ mol per liter for compounds of the general formula I or II is distinctly higher than that for fully synthetic HMG-CoA reductase inhibitors known from the literature, such as, for example, those described by G. E. Stokker et al., J. Med. Chem. 29, 170 (1986).

The enzyme HMG-CoA reductase is widespread in nature. It catalyzes the formation of mevalonic acid from HMG-CoA. This reaction is a central step in cholesterol biosynthesis (cf. J. R. Sabine in CRC Series in Enzyme Biology: 3-hydroxy-3-methylglutaryl Coenzyme A Reductase, CRS Press Inc. Boca Raten, Fla. 1983 (ISBN 0-8493-6551-1)).

A connection is drawn between high cholesterol levels and a number of disorders such as, for example, coronary heart disease or arteriosclerosis. Hence the lowering of elevated cholesterol levels is an aim of therapy for the prevention and treatment of disorders of these types. One starting point for this is the inhibition or reduction of endogenous cholesterol biosynthesis. Inhibitors of HMG-CoA reductase block cholesterol biosynthesis at an early stage.

Hence the compounds of the general formula I or II are suitable as hypolipidemics and for the treatment or prophylaxis of arteriosclerotic changes.

Hence the invention also relates to pharmaceutical products based on these compounds and to their use as medicaments, in particular as hypolipodemics and for the prophylaxis of arteriosclerotic changes.

The compounds of the formula I or II are used as hypolipidemics or anti-arteriosclerotics in oral doses of 3 to 2500 mg, but preferably in the dose range 10–500 mg. These daily doses can, where required, also be divided into two to four single doses or administered in sustained release form. The dosage regimen may depend on the type, age, weight, sex and medical condition of the patient.

An additional cholesterol-lowering effect can be achieved by concurrent administration of the compounds according to the invention with substances which bind bile acids, such as, for example, anion exchanger resins. Excretion of bile acids results in an increase in neosynthesis and thus in an increase in cholesterol breakdown (cf. M. S. Brown, P. T. Koranen and J. C. Goldstein, Science 212, 628 (1981); M. S. Brown, J. C. Goldstein, Spektrum der Wissenschaft 1985, 1, 96).

The compounds of the formula I or II, according to the invention, can be used in the form of the δ-lactones, as the free acids or in the form of their physiologically acceptable inorganic or organic salts or as esters. Acids and salts or esters can be used in the form of their aqueous solutions or suspensions, or dissolved or suspended in pharmacologically acceptable organic solvents such as monohydric or polyhydric alcohols such as, for example, ethanol, ethylene glycol or glycerol, in triacetin, in alcohol/acetaldehyde diacetal mixtures, oils such as, for example, sunflower oil or fish liver oil, ethers such as, for example, diethylene glycol dimethyl ether, or polyethers such as, for example, polyethylene glycol, or in the presence of other pharmacologically acceptable polymeric vehicles such as, for example, polyvinylpyrrolidone, or in solid formulations.

The preferred pharmaceutical forms for the compounds of the formula I or II are solid, can be administered orally and may contain the customary auxiliaries. They are produced by customary methods.

Particularly suitable formulations for oral use are tablets, coated tablets or capsules. One dosage unit preferably contains 10 to 500 mg of active substance.

The compounds of the formula III, V, VI and VII are new and represent valuable intermediates for the preparation of compounds of the formula I. Hence the invention also relates to these compounds and to processes for their preparation.

Preliminary note: Unless otherwise specified, NMR spectra were measured in CDCl$_3$ with TMS as internal standard. The following abbreviations are used to classify NMR signals: s=singlet, brs=broad singlet, d=doublet, t=triplet, q=quartet, h=heptet, mc=multiplet center, m=multiplet. Melting points are uncorrected. The following abbreviations are used for substituents: i=iso, t=tertiary, c=cyclo.

EXAMPLE 1

General procedure for the preparation of the compounds of the general formula X

Example 1a ($R^1=CH_3$, $R^2$=4-$FC_6H_4$, $R^3=CH_3$, $R^{10}=CH_3$)

Methyl 2-(1-oxoethyl)-3-(4-fluorophenyl)-5-oxohexanoate Xa

A solution of 1.2 g of potassium hydroxide in 12 ml of ethanol was added to 58.1 g (0.50 mol) of methyl acetoacetate. A solution of 41.0 g (0.25 mol) of 4-(4-fluorophenyl)but-3-en-2-one in 600 ml of ether was then slowly added dropwise in such a way that the temperature of the reaction mixture did not exceed 30° C. After the mixture had been stood at room temperature for three hours, it was diluted with 1 l of ether, and the pH was adjusted to 5 by addition of acetic acid. It was extracted by shaking successively with water and saturated $NaHCO_3$ solution, dried over $MgSO_4$ and evaporated. The residue was recrystallized from diisopropyl ether.

Yield: 50.6 g (72%).
Melting point: oil.
$^1$H NMR: δ/ppm=0.8–1.0 (m, 6H), 1.9 (s, 3H), 2.2–2.9 (m, 2H), 3.1–4.1 (m, 7H), 7.0–7.8 (m, 4H).

EXAMPLES 1b–1o

Compounds Xb–Xj and Xq–Xu were prepared in a manner analogous to that described in Example 1a (cf. Table 3)

TABLE 3

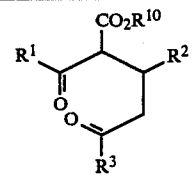

| Example | Compound | $R^1$ | $R^2$ | $R^3$ | $R^{10}$ | Yield % | $R_f$ Melting point °C. | $^1$H-NMR: δ/ppm = MS : m/e = |
|---|---|---|---|---|---|---|---|---|
| b | X b | $CH_3$ | 4-$ClC_6H_4$ | $CH_3$ | $CH_3$ | 78 | $0.42^a$ oil | 0.8–1.0 (m,6H), 2.0 (s,3H) 2.1 (S,3H), 2.2–2.9 (m,1H), 4.2 (m,7H), 7.4 (mc,4H). 299,297 ($M^+$ + H). |
| c | X c | $CH_3$ | 4-$FC_6H_4$ | $C_6H_5$ | $CH_3$ | 73 | $0.52^a$ oil | 0.8–1.0 (m,6H), 2.0 (s,3H), 2.2–2.9 (m,1H), 3.1–4.2 (m,7H), 6.9–8.0 (m,9H), 343 ($M^+$ + H). |
| d | X d | $iC_3H_7$ | 4-$FC_6H_4$ | $CH_3$ | $C_2H_5$ | 67 | $0.26^b$ oil | 0.8–1.3 (m,9H), 2.1 (S,3H), 2.2–2.9 (m,1H), 3.2–4.2 (m,6H), 6.8–7.6 (m,5H) 309 ($M^+$ + H). |
| e | X e | $iC_3H_7$ | 4-$FC_6H_4$ | $C_6H_5$ | $C_2H_5$ | 69 | $0.23^b$ oil | 0.6–1.3 (m,9H), 2.2–2.9 (m,1H), 3.2–3.6 (m,2H), 3.3–4.4 (m,4H), 6.8–9.0 (m,9H) 385 ($M^+$ + H). |
| f | X f | 4$FC_6H_4$ | $iC_3H_7$ | $C_6H_5$ | $CH_3$ | 71 | $0.38^c$ 60 | 0.7–1.1 (m,6H)) 1.6–2.1 (m,1H), 2.9–3.4 (m,2H), 3.6 (s,3H), 4.0–4.8 (m, 2H), 7.0–7.7 (m, 5H), 7.9–8.2 m,4H). 370 ($M^+$) |
| g | X g | $tC_4H_9$ | 4-$FC_6H_4$ | $C_2H_5$ | $C_6H_5$ | 67 | — 97–100 | 0.9–1.4 (m,12H), 3.2–3.6 (m,2H), 3.7–4.5 (m,4H), 6.6–8.0 (m,9H). 399 ($M^+$ + H) |
| h | X h | $iC_3H_7$ | 4-$CH_3OC_6H_4$ | $C_6H_5$ | $C_2H_5$ | 75 | $0.32^c$ 81 | 0.6–2.1 (m,9H), 2.1–2.8 (m,1H), 3.2–3.5 (m,2H), 3.8 (s,3H), 3.9–4.4 (m,4H), 7.0 (m,4H), 7.3–7.6 (m,3H), 7.8–8.0 (m,2H) 396 ($M^+$) |
| i | X i | $iC_3H_7$ | 4-F-$C_6H_4$ | 2,5($CH_3)_2$—$C_6H_3$ | $C_2H_5$ | 87 | $0.44^c$ oil | 0.6–1.4 (m,9H), 2.1 (s,3H), 2.4 (s,3H), 2.5–2.9 (m,1H), 3.1–3.4 (m,2H), 3.7–4.4 (m, 4H), 6.8–7.4 (m,7H) 413 ($M^+$ + H) |
| j | X j | $iC_3H_7$ | 4-$FC_6H_4$ | 4-$FC_6H_4$ | $C_2H_5$ | 70 | $0.63^a$ 122 | 0.7–1.4 (m,9H), 2.2–2.9 (m, 1H), 3.2–3.6 (m,2H), 3.9–4.4 (m,4H), 6.8–7.4 (m,6H), 7.9–8.1 (m,2H) |
| k | X q | $iC_3H_7$ | 4-$FC_6H_4$ | $iC_3H_7$ | $C_2H_5$ | 61 | $0.25^e$ 49–51 | 0.7–1.4 (m,15H), 2.4 (mc, 2H), 2.9 (mc,2H), 3.8–4.4 (m,4H), 7.1 (mc,4H) 351 ($M^+$ + H) |

TABLE 3-continued

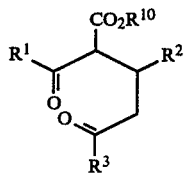

| Example | Compound | R$^1$ | R$^2$ | R$^3$ | R$^{10}$ | Yield % | R$_f$ Melting point °C. | $^1$H-NMR: δ/ppm = MS : m/e = |
|---|---|---|---|---|---|---|---|---|
| l | X r | iC$_3$H$_7$ | 4-FC$_6$H$_4$ | tC$_4$H$_5$ | C$_2$H$_5$ | 55 | 0.25$^e$ | 0.6–1.3 (m,18H), 2.3–3.1 (m,3H), 3.7–4.4 (m,4H), 6.9–7.2 (m,4H) |
|  |  |  |  |  |  |  | 72–75 | 307 (M$^+$ —C$_4$H$_9$) |
| m | X s | iC$_3$H$_7$ | 4-FC$_6$H$_4$ | cC$_6$H$_{11}$ | C$_2$H$_5$ | 47 | 0.58$^d$ | 0.8–1.9 (m,19H), 2.0–2.6 (m,2H), 2.7–3.0 (m,2H), 3.8–4.4 (m,4H), 6.8–7.4 (m,4H) |
|  |  |  |  |  |  |  | 99–101 | 391 (M$^+$ + H) |
| n | X t | C$_2$H$_5$ | 4-FC$_6$H$_4$ | C$_6$H$_5$ | C$_2$H$_5$ | 43 | 0.15$^d$ | 0.9–1.3 (m,6H), 2.0–2.8 (m,4H), 3.9–4.4 (m,4H), 6.9–7.6 (m,9H) |
|  |  |  |  |  |  |  | oil | 371 (M$^+$ + H) |
| o | X u | cC$_6$H$_{11}$ | 4-FC$_6$H$_4$ | C$_6$H$_5$ | C$_2$H$_5$ | 65 | 0.35(A); 0.3(B)$^d$ | A: 0.8–1.3 (m,9H), 1.5–1.8 (m,4H), 2.2 (mc,1H), 3.3–3.5 (m,2H), 4.1–4.3 (m,4H) 6.9 (mc,2H), 7.2–7.6 (m,6H), 7.9 (mc,2H) B: 1.0 (t,I=7Hz,3H), 1.2–1.9 (m,10H), 2.5 (mc,1H), 3.2–3.4 (m,2H), 3.9 (q,I=7Hz,2H), 4.2 (mc,2H), 6.9 (mc,2H), 7.1–7.6 (m,3H), 7.9 (mc,2H) |
|  |  |  |  |  |  |  | 137–139 (A) 108–110 (B) | 425 (M$^+$ + H) |

$^a$Cyclohexane/ethyl acetate 2:1
$^b$Cyclohexane/ethyl acetate 8:1
$^c$Cyclohexane/ethyl acetate 3:1
$^d$Cyclohexane/ethyl acetate 4:1
$^e$Cyclohexane/ethyl acetate 10:1

EXAMPLE 2

General procedure for the preparation of the compounds of the general formula XV (Z=CH) (cf. F. Rehberg, F. Krohnke, Liebigs Ann. Chem. 717, 91 (1968)) Example 2a (R$^1$=CH$_3$, R$^2$=4-FC$_6$H$_4$, R$^3$=CH$_3$, R$^{10}$=CH$_3$)

Methyl 2,6-dimethyl-4-(4-fluorophenyl)pyridine-3-carboxylate XVa

A suspension of 28.0 g (100 mmol) of methyl 3-(4-fluorophenyl)-2-(1-oxoethyl)-5-oxohexanoate (=Xa from Example 1), 120 g of ammonium acetate and 120 g of iron(III) chloride hexahydrate in 1000 ml of glacial acetic acid was refluxed, with stirring, until the precursor could no longer be detected by thin-layer chromatography (4 h). The mixture was cooled and then filtered, and the solid residue was washed with ethanol and toluene. The filtrate was evaporated and then the residue was suspended in water, the pH was adjusted to 8–9 by addition of solid sodium bicarbonate, and the mixture was extracted several times with ether. The combined extracts were washed with saturated NaCl, dried over MgSO$_4$ and evaporated. Purification of the crude product by column chromatography (silica gel, cyclohexane/ethyl acetate 2:1) provided 23.6 g (91%) of XVa in the form of white crystals.

Melting point 89°–90° C.

$^1$H NMR (CDCl$_3$; 60 MHz): δ=2.60 (s,6H), 3.66 (s,3H), 6.95–7.50 (m,5H) ppm.

MS: m/e=259 (M$^+$).

EXAMPLE 2b–2o

The compounds XVb–XVj and XVq–XVu were prepared in a manner analogous to that described in Example 2a (cf. Table 4)

TABLE 4

$$\underset{R^3}{\underset{\|}{N}}\overset{CO_2R^{10}}{\underset{Z}{\overset{R^2}{\|}}}R^1 \quad Z = CH$$

| Example | Compound | $R^1$ | $R^2$ | $R^3$ | $R^{10}$ | Yield % | $R_f$ Melting point °C. | $^1$H-NMR: δ/ppm = MS : m/e = |
|---|---|---|---|---|---|---|---|---|
| b | XVb | $CH_3$ | 4-$ClC_6H_4$ | $CH_3$ | $CH_3$ | 93 | 0.50$^a$ oil | 2.6 (s,6H), 3.7 (s,3H), 7.0 (s,1H), 7.4 (mc,4H). 277,275 ($M^+$) |
| c | XVc | $CH_3$ | 4-$FC_6H_4$ | $C_6H_5$ | $CH_3$ | 94 | 0.59$^a$ 134–135 | 2.7 (s,3H), 3.7 (s,3H), 7.0-8.1 (m,10H). 321 ($M^+$) |
| d | XVd | $iC_3H_7$ | 4-$FC_6H_4$ | $CH_3$ | $C_2H_5$ | 87 | 0.75$^b$ oil | 1.1 (t, J=7Hz,3H), 1.3 (d,J=7Hz,6H) 2.6 (s,3H), 3.2 (h,J=7Hz,1H), 4.1 (q,J=7Hz,2H), 7.0 (s,1H), 7.1-7.5 (m,4H). 301 ($M^+$) |
| e | XVe | $iC_3H_7$ | 4-$FC_6H_4$ | $C_6H_5$ | $C_2H_5$ | 99 | 0.75$^b$ oil | 1.1 (t,J=7Hz,3H), 1.3 (d,J=7Hz,6H), 3.3 (h, J=7Hz,1H), 4.2 (q,J=Hz, 2H), 7.0-7.6 (m,8H), 8.1-8.2 (m,2H). 363 ($M^+$) |
| f | XVf | 4-$FC_6H_4$ | $iC_3H_7$ | $C_6H_5$ | $CH_3$ | 73 | 0.50$^b$ oil | 1.3 (d, J=7Hz,6H), 3.2 (h,J=7Hz,1H), 3.7 (s,3H), 7.0-8.2 (m,10H). 349 ($M^+$) |
| g | XVg | $tC_4H_9$ | 4-$FC_6H_4$ | $C_6H_5$ | $C_2H_5$ | 85 | 0.66$^c$ oil | 1.0 (t,J=7Hz,3H), 1.4 (s,9H), 4.0 (q,J=7Hz,2H), 7.0-7.7 (m, 8H), 8.1-8.3 (m,2H) 378 ($M^+$+H) |
| h | XVh | $iC_3H_7$ | 4-$CH_3OC_6H_4$ | $C_6H_5$ | $C_2H_5$ | 88 | 0.54$^c$ 72–74 | 1.1 (t,J=7Hz,3H), 1.4 (d, J=7Hz,6H), 3.2 (h,J=7Hz,1H), 3.9 (s,3H), 4.2 (q,J=7Hz,2H), 6.9-7.6 (m,8H), 8.0-8.2 (m,2H) 376 ($M^+$+H) |
| i | XVi | $iC_3H_7$ | 4-$FC_6H_4$ | 2,5-$(CH_3)_2C_6H_3$ | $C_2H_5$ | 91 | 0.63$^c$ oil | 1.1 (t,J=7Hz,3H), 1.4 (d, J=7Hz,6H), 2.4 (s,3H), 2.5 (s,3H), 3.2 (h,J=7Hz,1H), 4.2 (q,J=Hz,2H), 7.0-7.6 (m,8H) 392 ($M^+$+H) |
| j | XVj | $iC_3H_7$ | 4-$FC_6H_4$ | 4-$FC_6H_4$ | $C_2H_5$ | 78 | 0.58$^c$ 112–114 | 1.1 (t,J=7Hz,3H), 1.4 (d, J=7Hz,6H), 3.2 (h,J=7Hz,1H), 4.2 (q,J=7Hz,2H), 7.0-7.6 (m,7H), 8.0-8.3 (m,2H) 381 ($M^+$+H) |
| k | XVq | $iC_3H_7$ | 4-$FC_6H_4$ | $iC_3H_7$ | $C_2H_5$ | 89 | 0.73$^d$ | 1.1 (t,J=7Hz,3H), 1.3 (d, J=7Hz,12H), 3.1 (mc,2H), 4.1 (q,J=7Hz,2H), 7.0 (s, 1H), 7.2 (mc,4H) |
| l | XVr | $iC_3H_7$ | 4-$FC_6H_4$ | $tC_4H_9$ | $C_2H_5$ | 81 | 0.83$^c$ oil | 0.9-1.4 (m,18H), 3.1 (h, J=7Hz,1H), 4.1 (q,J=7Hz, 2H), 7.0-7.5 (m,5H) 344 ($M^+$+H) |
| m | XVs | $iC_3H_7$ | 4-$FC_6H_4$ | $cC_6H_{11}$ | $C_2H_5$ | 96 | 0.76$^c$ oil | 1.0 (t,J=7Hz,3H), 1.2-2.1 (m,16H), 2.5-3.4 (m,2H), 4.1 (q,J=7Hz,2H), 7.0 (s, 1H), 7.2 (mc,2H) 369 ($M^+$) |
| n | XVt | $C_2H_5$ | 4-$FC_6H_4$ | $C_6H_5$ | $C_2H_5$ | 65 | 0.46$^d$ oil | 1.1 (t,J=7Hz,3H), 1.4 (t, J=7Hz,3H), 3.0 (q,J=7Hz, 2H), 4.1 (q,J=7Hz,2H), 7.1 (mc,2H), 7.4-7.6 (m, 6H), 8.1 (mc,2H) 350 ($M^+$+H) |
| o | XVu | $cC_6H_{11}$ | 4-$FC_6H_4$ | $C_6H_5$ | $C_2H_5$ | 84 | 0.55$^d$ oil | 1.1 (t,J=7Hz,3H), 1.1-2.0 (m,10H), 2.4-3.0 (m,1H), 4.2 (q,J=7Hz,2H), 7.0-7.6 (m,8H), 8.1 (m,2H) |

TABLE 4-continued

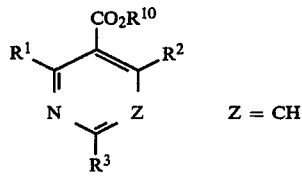

Z = CH

| Example | Compound | R¹ | R² | R³ | R¹⁰ | Yield % | $R_f$ Melting point °C. | ¹H-NMR: δ/ppm = MS : m/e = |
|---|---|---|---|---|---|---|---|---|
| | | | | | | | | 404 (M⁺+H) |

[a] Cyclohexane/ethyl acetate 1:1
[b] Cyclohexane/ethyl acetate 3:1
[c] Cyclohexane/ethyl acetate 8:1
[d] Cyclohexane/ethyl acetate 4:1

EXAMPLE 3

General procedure for the preparation of compounds of the general formula XIV

Example 3a (R¹=iC₃H₇, R²=4-FC₆H₄, R³=C₆H₅, R¹⁰=C₂H₅)

Ethyl 1,4-dihydro-4-(4-fluorophenyl)-2-(1-methylethyl)-6-phenylpyrimidine-3-carboxylate XIVo Route A 98.6 g (0.62 mol) of methyl 4-methyl-3-oxopentanoate (corresponds to the general formula IX, scheme 1) were dissolved in 400 ml of toluene, and 77.0 g of 4-fluorobenzaldehyde XIa, 6.8 g of piperazine and 7.3 g of caproic acid were added. The reaction mixture was boiled under reflux with a water trap until no more water of reaction was formed (24 h) and was then extracted by shaking three times with saturated sodium bicarbonate solution, three times with 5% strength acetic acid and once with water. The organic phase was dried over magnesium sulfate and then evaporated. 150 g (<0.58 mol) of crude XIIa remained, and this was dissolved in 1700 ml of toluene, and 102.2 g (0.85 mol) of benzamidine.HCl.H₂O XIIIa and 90.7 g (0.94 mol) of potassium acetate were added successively. This mixture was boiled under reflux with a water trap until formation of water of reaction was finished (24 h) and was then washed with sodium bicarbonate solution, 5% strength acetic acid and water, dried over magnesium sulfate and evaporated.

The resulting crude product (78 g) was filtered through silica gel (mobile phase cyclohexane/ethyl acetate 4:1).

Yield: 72.6 g (63%) XIVo as a yellow oil.

Rf: (cyclohexane/ethyl acetate 2:1): 0.31.

¹H NMR: δ/ppm=1.2 (t,J=7 Hz, 3H), 1.3 (d,J=7 Hz, 6H), 4.0–4.5 (m,3H), 5.8 (s,1H), 7.0–7.9 (m,10H).

Route B 98.6 g (0.62 mol) of ethyl 4-methyl-3-oxopentanoate (IXa) 77.0 g (0.62 mol) of 4-fluorobenzaldehyde XIa, 102 g (0.85 mol) of benzamidine.HCl.H₂O (XIIIa) and 90.7 g (0.94 mol) of potassium acetate were mixed in 1500 ml of toluene and the mixture was refluxed with a water trap for 24 h. Working-up and purification as described for Route A provided XIVo as a yellow oil.

Yield: 110 g (55%).

Rf: cf. route A.

¹H NMR: cf. route A.

EXAMPLE 3b–3h

Compounds XIVk–XIVn, XIVp, XIVv and XIVw were prepared in a manner analogous to that described in Example 3a (cf. Table 5)

TABLE 5

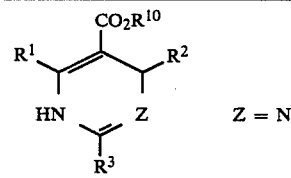

Z = N

| Example | Compound | R¹ | R² | R³ | R¹⁰ | Yield | $R_f$ Melting point °C. | ¹H-NMR: δ/ppm = MS : m/e = |
|---|---|---|---|---|---|---|---|---|
| b | XIVk | CH₃ | 4-FC₆H₄ | CH₃ | C₂H₅ | 57 | 0.30[a] oil | 1.1 (t,J=7Hz,3H), 2.0 (s,3H), 2.3 (s,3H), 4.0 (q, J=7Hz,2H), 5.5 (s,1H), 6.7–7.5 (m,4H). 276(M⁺) |
| c | XIVl | CH₃ | 4-ClC₆H₄ | CH₃ | C₂H₅ | 49 | 0.25[a] oil | 1.1 (t,J=7Hz,3H), 2.1 (s,3H), 2.3 (s,3H), 4.0 (q,J=7Hz,2H) 5.5 (s,1H), 6.7–7.5 (m,4H) 294,292 (M⁺) |
| d | XIVm | CH₃ | cC₆H₁₁ | CH₃ | C₂H₅ | 61 | 0.35[a] oil | 264 (M⁺) |
| e | XIVn | CH₃ | 4-ClC₆H₄ | H | CH₃ | 39 | 0.28[a] oil | 2.3 (s,3H), 3.6 (s,3H), 7.1–7.4 (m,4H). 266,264 (M⁺) |
| f | XIVp | iC₃H₇ | 4-FC₆H₄ | CH₃ | C₂H₅ | | 0.24[b] | 276 (M⁺) |

TABLE 5-continued

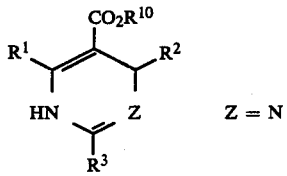

Z = N

| Example | Compound | R¹ | R² | R³ | R¹⁰ | Yield | Rf Melting point °C. | ¹H-NMR: δ/ppm = MS : m/e = |
|---|---|---|---|---|---|---|---|---|
| g | XIVv | iC₃H₇ | 4-FC₆H₄ | iC₃H₇ | C₂H₅ | 46 | oil 0.39ᶜ 115–117° | 328 (M⁺) |
| h | XIVw | iC₃H₇ | 4-FC₆H₄ | 4-FC₆H₄ | C₂H₅ | 80 | 0.39ᶜ oil | 384 (M⁺) |

ᵃDichloromethane/methanole 9:1
ᵇEthyl acetate
ᶜCyclohexane/ethyl acetate 2:1

EXAMPLE 4

General procedure for the preparation of compounds of the general formula XV (Z=N)

Example 4a (R¹=iC₃H₇, R²=4-FC₆H₄, Rqhu 3=C₆H₅, R¹⁰=C₂H₅)

Ethyl 4-(4-fluorophenyl)-2-(1-methylethyl)-6-phenyl-pyrimidine-3-carboxylate XVo 24.2 g (66.0 mmol) of ethyl 1,4-dihydro-4-(4-fluorophenyl)-2-(1-methylethyl)-6-phenylpyrimidine-3-carboxylate XIVo (of Example 3a) were dissolved in 300 ml of toluene, 18.0 g (790 mmol) of 2,3-dichloro-5,6-dicyano-1,4-benzoquinone (=DDQ) were added, and the mixture was heated to 50° C. with stirring. After 3 h, the solvent was removed in vacuo, and the residue was extracted several times with a 4:1 mixture of cyclohexane and ethyl acetate. The organic extracts were evaporated once more. The residue was purified by filtration through silica gel (cyclohexane/ethyl acetate 4:1).

Yield: 19.95 g of XVo (82%) as white crystals.
Rf (cyclohexane/ethyl acetate 4:1) 0.73.
Melting point: 105° C.
¹H NMR δ/ppm=1.1 (t,J=7 Hz, 3H), 1.4 (d,J=7 Hz, 6H), 3.2 (h,J=7 Hz, 1H), 4.2 (q,J=7 Hz, 2H), 7.0–8.0 (m,7H), 8.5–8.8 (m,2H).

EXAMPLE 4b–4h

Compounds XVk–XVn, XVp, XVv and XVw were prepared in a manner analogous to that described in Example 4a (cf. Table 6).

TABLE 6

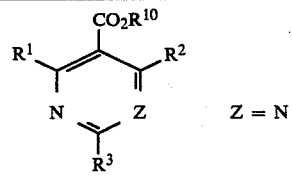

Z = N

| Example | Compound | R¹ | R² | R³ | R¹⁰ | Yield % | Rf Melting point °C. | ¹H-NMR: δ/ppm = MS : m/e = |
|---|---|---|---|---|---|---|---|---|
| b | XVk | CH₃ | 4-FC₆H₄ | CH₃ | C₂H₅ | 59 | 0.86ᵃ oil | 1.1(t,J=7Hz,3H),2.6 (s,3H), 2.7 (s,3H), 4.2 (q,J=7Hz,2H), 7.0–7.9 (m,4H). 274 (M⁺) |
| c | XVl | CH₃ | 4-ClC₆H₄ | CH₃ | C₂H₅ | 60 | 0.72ᵃ oil | 1.1 (t,J=7Hz,3H), 2.6 (s,3H), 4.2 (q,J=7Hz, 3H), 7.2–7.8 (m,4H). 292,290 (M⁺) |
| d | XVm | CH₃ | cC₆H₁₁ | CH₃ | C₂H₅ | 63 | 0.77ᵃ oil | 1.1–2.0 (m,13H), 2.5 (s,3H), 2.6 (mc,1H), 2.7 (s,3H), 4.4(q,J=7Hz,2H). 262 (M⁺) |
| e | XVn | CH₃ | 4-ClC₆H₄ | H | CH₃ | 46 | 0.65ᵃ oil | 2.6 (s,3H), 3.8 (s,3H), 7.2–7.8 (m,4H), 9.2 (2,1H). 266,264 (M⁺) |
| f | XVp | iC₃H₇ | 4-FC₆H₄ | CH₃ | C₂H₅ | 59 | oil | 1.1 (t,J=7Hz,3H), 1.4 (d, J=7Hz,6H), 2.7 (s,3H), 3.2 (h,J=7Hz,1H), 4.1 (q, J=7Hz,2H), 7.0–7.9 (m,4H) 290 (M⁺) |
| g | XVv | iC₃H₇ | 4-FC₆H₄ | iC₃H₇ | C₂H₅ | 79 | 0.87ᶜ oil | 1.1 (t,3H), 1.25 (d,6H); 1.4 (d,6H), 3.2 (H,2H), 4.2 (q,2H), 7.0–7.9 (m,4H) 330 (M⁺) |
| h | XVw | iC₃H₇ | 4-FC₆H₄ | 4-FC₆H₄ | C₂H₅ | 66,5 | 0.58ᶜ | 386 (M⁺) |

TABLE 6-continued

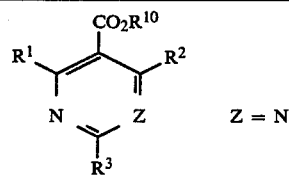

Z = N

| Example | Compound | R¹ | R² | R³ | R¹⁰ | Yield % | $R_f$ Melting point °C. | ¹H-NMR: δ/ppm = MS : m/e = |
|---|---|---|---|---|---|---|---|---|
| | | | | | | | oil | |

[a]Dichloromethane/methanol 9:1
[b]Cyclohexane/ethyl acetate 4:1
[c]Cyclohexane/ethyl acetate 2:1

EXAMPLE 5

General procedure for the preparation of compounds of the general formula XVI

Example 5a (R¹=CH₃, R²=4-FC₆H₄, R³=CH₃, Z=CH) 2.6-Dimethyl-4-(4-fluorophenyl)pyridin-3-ylmethanol XVIa 30 ml (30 mmol) of a 1.0M solution of lithium aluminum hydride in tetrahydrofuran were added dropwise to a solution of 7.8 g (30.1 mmol) of methyl 2,6-dimethyl-4-(4-fluorophenyl)pyridine-3-carboxylate XVa (from Example 2) in 40 ml of tetrahydrofuran, with exclusion of moisture. After the mixture had then been stirred for 1.5 hours, it was poured onto water, the mixture was extracted several times with ether, and the ether was washed with water, dried over MgSO₄ and evaporated. The remaining crude XVIa was washed with a 1:1 mixture of cyclohexane and ethyl acetate.

Yield: 6.5 g (93%).
Melting point: 124° C.
¹H NMR (CDCl₃; 60 MHz): δ=2.0 (s,1H); 2.5 (s,3H); 2.7 (s,3H); 4.6 (s,2H); 6.9 (s,1); 7.0–7.5 (m,4H) ppm.
MS: m/e=231 (M⁺).

EXAMPLES 5b–5w

Compounds XVIb–XVIw were prepared in a manner analogous to that described in Example 5a (cf. Table 7)

TABLE 7

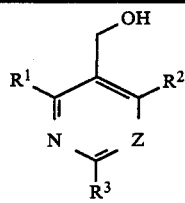

| Example | Compound | Z | R¹ | R² | R³ | Yield % | $R_f$ Melting point °C. | ¹H-NMR: δ/ppm = MS: m/e = |
|---|---|---|---|---|---|---|---|---|
| b | XVIb | CH | CH₃ | 4-ClC₆H₄ | CH₃ | 78 | 0.10[a] 180 | 1.7(brs, 1H), 2.5(s, 3H), 4.4(s, 2H), 6.9(s, 1H), 7.4(mc, 4H). 249, 247(M⁺) |
| c | XVIc | CH | CH₃ | 4-FC₆H₄ | C₆H₅ | 73 | 0.16[a] 185 | 2.8(s, 3H), 4.1(s, 1H), 4.6(s, 2H), 7.0–8.1 (m, 10H). 293(M⁺) |
| d | XVId | CH | iC₃H₇ | 4-FC₆H₄ | CH₃ | 67 | 0.92[a] oil | 1.4(d, J=7Hz, 6H), 1.6 (brs, 1H), 2.6(s, 3H), 3.6 (h, J=7Hz, 1H), 4.6(s, 2H), 6.9(s, 1H), 7.0–7.6(m, 4H) 259(M⁺) |
| e | XVIe | CH | iC₃H₇ | 4-FC₆H₄ | C₆H₅ | 69 | 0.33[b] 176 | 1.4(d, J=7Hz, 6H), 1.5 (brs, 1H), 3.6(h, J=7Hz, 1H) 4.5(s, 2H), 7.0–7.6(m, 8H), 8.0–8.2(m, 2H). 321(M⁺) |
| f | XVIf | CH | 4-FC₆H₄ | iC₃H₇ | C₆H₅ | 79 | 0.20[b] 157 | 1.4(d, J=7Hz, 6H), 1.7 (brs, 1H), 3.5(h, J=7Hz, 1H), 4.7(s, 2H), 7.0–8.2(m, 10H) 322(M⁺ +H) |
| g | XVIg | CH | tC₄H₉ | 4-FC₆H₄ | C₆H₅ | 88 | 0.40[b] oil | 1.4(s, 9H), 4.6(s, 2H), 7.0–7.6(m, 8H), 8.1–8.3 (m, 2H) 336(M⁺ +H) |
| h | XVIh | CH | iC₃H₇ | 4-CH₃OC₆H₄ | C₆H₅ | 93 | 0.26[b] | 1.4(d, J=7Hz, 6H), 1.5 (s, 1H), 3.6(h, J=7Hz, 1H), 3.9(s, 3H), 4.7(s, 2H), 7.0–7.6(m, 8H), 8.1–8.3 |

TABLE 7-continued

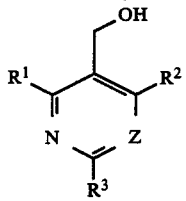

| Example | Compound | Z | R[1] | R[2] | R[3] | Yield % | $R_f$ Melting point °C. | $^1$H-NMR: δ/ppm = MS: m/e = |
|---|---|---|---|---|---|---|---|---|
| i | XVIi | CH | $iC_3H_7$ | $4\text{-}FC_6H_4$ | $2,5\text{-}(CH_3)_2C_6H_3$ | 89 | 173–175 0.48[b] | (m, 2H) 334($M^+$+H) 1.4(d, J=7Hz, 6H), 1.6(brs, 1H), 2.3(s, 3H), 2.4(2, 3H), 3.6(h, J=7Hz, 1H), 4.7(s, 2H) 7.0–7.6(m, 8H) |
| j | XVIj | CH | $iC_3H_7$ | $4\text{-}FC_6H_4$ | $4\text{-}FC_6H_4$ | 92 | oil 0.40[b] | 350($M^+$+H) 1.4(d, J=7Hz, 6H), 1.6(brs, 1H), 3.6(h, J=7Hz, 1H), 4.8 (s, 2H), 7.0–7.6(m, 7H), 8.0–8.3(m, 2H) |
| k | XVIk | N | $CH_3$ | $4\text{-}FC_6H_4$ | $CH_3$ | 85 | 174–176 0.52[c] | 340($M^+$+H) 2.6(s, 3H), 2.7(s, 3H), 4.6(s, 2H), 7.0–7.9(m, 4H). |
| l | XVIl | N | $CH_3$ | $4\text{-}ClC_6H_4$ | $CH_3$ | 69 | oil 0.51[c] | 232($M^+$) 2.0(brs, 1H), 2.6(s, 3H), 2.7(s, 3H), 4.7(s, 2H), 7.1–7.8(m, 4H) |
| m | XVIm | N | $CH_3$ | $cC_6H_{11}$ | $CH_3$ | 59 | oil 0.59[c] | 250, 248($M^+$) 1.0–2.0(m, 12H), 2.4 (s, 3H), 2.5(s, 3H), 4.7 (s, 2H). |
| n | XVIn | N | $CH_3$ | $4\text{-}ClC_6H_4$ | H | 72 | oil 0.37[c] | 220($M^+$) 2.7(s, 3H), 4.7(s, 2H), 7.2–7.9(m, 4H), 9.1(s, 1H). |
| o | XVIo | N | $iC_3H_7$ | $4\text{-}FC_6H_4$ | $C_6H_5$ | 88 | oil 0.29[b] | 1.5(d, J=7Hz, 6H), 3.6 (h, J=7Hz, 1H), 4.8(s, 2H), 7.1–8.8(m, 9H) |
| p | XVIp | iN | $iC_3H_7$ | $4\text{-}FC_6H_4$ | $CH_3$ | | oil 0.24[b] | 306($M^+$) 1.5(d, J=7Hz, 6H), 2.7(s, 3H), 3.5(h, J=7Hz, 1H), 4.7 (s, 2H), 7.1–8.5(m, 4H) |
| q | XVIq | CH | $iC_3H_7$ | $4\text{-}FC_6H_4$ | $iC_3H_7$ | 91 | oil 0.56[b] | 260($M^+$) 1.3(d, J=7Hz, 6H), 1.4(dJ= 7Hz, 6H) 1.5(s, 1H), 3.1 (h, J=7Hz, 1H), 3.5(h, J= 7Hz, 1H), 4.6(s, 2H), 6.9–7.5(m, 5H) |
| r | XVIr | CH | $iC_3H_7$ | $4\text{-}FC_6H_4$ | $tC_4H_9$ | 95 | 90 0.36[d] | 288($M^+$+H) 1.3(d, J=7Hz, 6H), 1.4(s, 9H), 1.6(s, 1H), 3.4(h, J= 7Hz, 1H), 4.6(s, 2H), 7.0 (s, 1H), 7.1–7.6(m, 4H) |
| s | XVIs | CH | $iC_3H_7$ | $4\text{-}FC_6H_4$ | $cC_6H_{11}$ | 76 | oil 0.52[b] | 301($M^+$) — |
| t | XVIt | CH | $C_2H_5$ | $4\text{-}FC_6H_4$ | $C_6H_5$ | 100 | oil 0.18[b] | 327($M^+$) 1.5(t, J=7Hz, 3H), 1.6(s, 1H), 3.1(q, J=7Hz, 2H), 4.5 (s, 2H), 7.1–7.6(m, 8H), 8.0–8.2(m, 2H) |
| u | XVIu | CH | $cC_6H_{11}$ | $4\text{-}FC_6H_4$ | $C_6H_5$ | 78 | oil 0.4[b] | 308($M^+$+H) 1.0–2.1(m, 11H), 2.9–3.5 (m, 1H), 4.6(s, 2H), 7.0–7.6 (m, 8H), 8.0–8.3(m, 2H) |
| v | XVIv | N | $iC_3H_7$ | $4\text{-}FC_6H_4$ | $iC_3H_7$ | 81 | 181–183 0.47[b] | 361($M^+$) 4.6(s, 2H), 1.6(s, 1H) |
| w | XVIw | N | $iC_3H_7$ | $4\text{-}FC_6H_4$ | $4\text{-}FC_6H_4$ | 58 | oil 0.40[b] 177 | — 340($M^+$) |

[a]Cyclohexane/ethyl acetate 1:1
[b]Cyclohexane/ethyl acetate 4:1
[c]Dichloromethane/methanol 9:1
[d]Cyclohexane/ethyl acetate 10:1

EXAMPLE 6

General procedure for the preparation of compounds of the general formula XVII

Example 6a ($R^1$=$CH_3$, $R^2$=4-$FC_6H_4$, $R^3$=$CH_3$, Z=CH, X-Br)

2,6-Dimethyl-4-(4-fluorophenyl)pyridin-3-ylmethyl bromide XVIIa 5.3 ml (54.4 mmol) of phosphorus tribromide were added dropwise to a solution of 6.4 g (27.7 mmol) of 2,6-dimethyl-4-(4-fluorophenyl)pyridin-3-ylmethanol XVIa in a mixed solvent composed of 50 ml of toluene and 25 ml of dichloromethane, and the mixture was stirred at room temperature for 1 h. The mixture was added to saturated $NaHCO_3$ solution and extracted by shaking several times with ether. The combined organic extracts were washed with water, dried over $MgSO_4$ and evaporated. 6.4 g (79%) of XVIIa remained and could be reacted further without purification.

Melting point: 86°–87° C.

$^1$H NMR ($CDCl_3$; 60 MHz): δ=2.5 (s,3H); 2.7 (s,3H); 4.4 (s,2H); 6.9 (s,1H); 7.0–7.5 (m,4H) ppm.

MS: m/e=295, 293 ($M^+$).

EXAMPLE 6b–6w

The compounds XVIIb–XVIIw were prepared in a manner analogous to that described in Example 6a (cf. Table 8)

TABLE 8

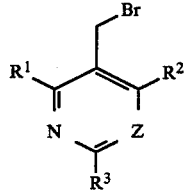

| Example | Compound | Z | $R^1$ | $R^2$ | $R^3$ | Yield % | $R_f$ Melting point °C. | $^1$H-NMR: δ/ppm = MS: m/e = |
|---|---|---|---|---|---|---|---|---|
| b | XVIIb | CH | $CH_3$ | 4-$ClC_6H_4$ | $CH_3$ | 76 | 0.44$^a$ | 2.5(s, 3H), 2.7(s, 3H), 4.6(s, 2H), 6.9(s, 1H), 7.4(mc, 4H). |
| | | | | | | | oil | 313, 311, 309($M^+$) |
| c | XVIIc | CH | $CH_3$ | 4-$FC_6H_4$ | $C_6H_5$ | 94 | 0.78$^a$ | 2.8(s, 3H), 4.5(s, 2H), 7.1–8.1(m, 10H). |
| | | | | | | | 156–158 | 357, 355($M^+$) |
| d | XVIId | CH | $iC_3H_7$ | 4-$FC_6H_4$ | $CH_3$ | 67 | 0.92$^a$ | 1.4(d, J=7Hz, 6H), 2.5 (s, 3H), 3.5(h, J=7Hz, 1H), 4.4(s, 2H), 6.8(s, 1H), 7.0–7.6(m, 4H). |
| | | | | | | | oil | 323, 321($M^+$) |
| e | XVIIe | CH | $iC_3H_7$ | 4-$FC_6H_4$ | $C_6H_5$ | 73 | 0.86$^b$ | 1.3(d, J=7Hz, 6H), 3.5 (h, J=7Hz, 1H), 4.4(s, 2H) 7.0–7.6(m, 8H), 8.0–8.2 (m, 2H). |
| | | | | | | | oil | 385, 383($M^+$) |
| f | XVIIf | CH | 4-$FC_6H_4$ | $iC_3H_7$ | $C_6H_5$ | 69 | 0.72$^b$ | 1.4(d, J=7Hz, 6H), 3.5(h, J=7Hz, 1H), 4.6(s, 2H), 7.0–8.2(m, 10H) |
| | | | | | | | 122 | 386, 384($M^+$+H) |
| g | XVIIg | CH | $tC_4H_9$ | 4-$FC_6H_4$ | $C_6H_5$ | 83 | 0.84$^c$ | 1.4(s, 9H), 4.2(s, 2H), 7.0–7.6(m, 8H), 8.0–8.2 (m, 2H) |
| | | | | | | | oil | 400, 398($M^+$+H) |
| h | XVIIh | CH | $iC_3H_7$ | 4$CH_3OC_6H_4$ | $C_6H_5$ | 78 | 0.75$^c$ | 1.5(d, J=7Hz, 6H), 3.6 (h, J=7Hz, 1H), 3.9(s, 3H), 4.5(s, 2H), 7.0–7.6(m, 8H) 8.1–8.2(m, 2H) |
| | | | | | | | 103–105 | 398, 396 ($M^+$+H) |
| i | XVIIi | CH | $iC_3H_7$ | 4-$FC_6H_4$ | 2,5-$(CH_3)_2C_6H_3$ | 71 | 0.80$^c$ | 1.3(d, J=7Hz, 6H), 2.3(s, 3H), 2.4(s, 3H), 3.5(h, J=7Hz, 1H), 4.4(s, 2H), 6.9–7.5(m, 8H) |
| | | | | | | | oil | 414, 412($M^+$+H) |
| j | XVIIj | CH | $iC_3H_7$ | 4-$FC_6H_4$ | 4-$FC_6H_4$ | 89 | 0.87$^c$ | 1.4(d, J=7Hz, 6H), 3.5 (h, J=7Hz, 1H), 4.5(s, 2H), 7.0–7.6(m, 7H), 8.0–8.2 (m, 2H) |
| | | | | | | | 111–113 | 401, 399($M^+$) |
| k | XVIIk | N | $CH_3$ | 4-$FC_6H_4$ | $CH_3$ | 59 | 0.60$^d$ | 2.6(s, 3H), 2.7(s, 3H), 4.5(s, 2H), 7.0–7.9 (m, 4H) |
| | | | | | | | oil | 295($M^+$+H) |
| l | XVIIl | N | $CH_3$ | 4-$ClC_6H_4$ | $CH_3$ | 87 | 0.65$^d$ | 2.7(s, 3H), 2.8(s, 3H), 4.5(s, 2H), 7.0–7.9(m, 4H) |
| | | | | | | | 112 | 315, 313, 311($M^+$+H) |
| m | XVIIm | N | $CH_3$ | $cC_6H_{11}$ | $CH_3$ | 82 | 0.75$^d$ | 1.0–2.0(m, 11H), 2.4(s, 3H), 2.5(s, 3H), 4.5(s, 2H). |
| | | | | | | | oil | 274, 272($M^+$) |
| n | XVIIn | N | $CH_3$ | 4-$ClC_6H_4$ | H | 91 | 0.50$^c$ | 2.8(S, 3H), 4.7(s, 2H), |

TABLE 8-continued

Structure: R¹ and R² attached to a carbon bearing CH₂Br group, with N=C(R³)—Z ring system

| Example | Compound | Z | R¹ | R² | R³ | Yield % | $R_f$ Melting point °C. | ¹H-NMR: δ/ppm = MS: m/e = |
|---|---|---|---|---|---|---|---|---|
| o | XVIIo | N | iC₃H₇ | 4-FC₆H₄ | C₆H₅ | 84 | oil 0.73$^c$ | 7.2–7.9(m, 4H), 9.0(s, 1H) 298, 296(M⁺) 1.4(d, J=7Hz, 6H), 3.6(h, J=7Hz, 1H), 4.6(s, 2H), 7.1–8.6(m, 9H) |
| p | XVIIp | N | iC₃H₇ | 4-FC₆H₄ | CH₃ | 79 | 134 0.56$^d$ | 386, 384(M⁺) 1.5(d, J=7Hz, 6H), 2.6(s, 3H), 3.4(h, J=7Hz, 1H), 4.5(s, 2H), 7.0–8.1(m, 4H) |
| q | XVIIq | CH | iC₃H₇ | 4-FC₆H₄ | iC₃H₇ | 86 | oil 0.95$^c$ | 324, 322(M⁺) 1.3(d, J=7Hz, 6H), 1.4(d, J=7Hz, 6H), 3.1(h, J=7Hz, 1H), 3.5(h, J=7Hz, 1H)4.5 4.5(s, 2H), 6.9(s, 1H), 7.0–7.6(m, 4H) |
| r | XVIIr | CH | iC₃H₇ | 4-FC₆H₄ | tC₄H₉ | 90 | 81 0.87$^e$ | 352, 350(M⁺+H) 1.3(s, 9h), 1.3(d, J=7Hz, 6H), 3.5(h, J=7Hz, 1H), 4.4(s, 2H), 7.0–7.6(m, 5H) |
| s | XVIIs | CH | iC₃H₇ | 4-FC₆H₄ | cC₆H₁₁ | 86 | oil 0.89$^e$ | 365, 363(M⁺) 1.4(d, J=7Hz, 6H), 1.4–2.1 (m, 10H), 2.7(mc, 1H), 3.5 (h, J=7Hz, 1H), 4.5(s, 2H), 6.9–7.6(m, 5H) |
| t | XVIIt | CH | C₂H₅ | 4-FC₆H₄ | C₆H₅ | 97 | 84–86 0.57$^c$ | 391, 389(M⁺) 1.5(t, J=7Hz, 3H), 3.1(q, J=7Hz, 2H), 4.5(s, 2H), 7.1–7.6(m, 8H), 8.1(mc, 2H) |
| u | XVIIu | CH | cC₆H₁₁ | 4-FC₆H₄ | C₆H₅ | 93 | 120 0.53$^c$ | 371, 369(M⁺) 1.2–2.3(m, 11H), 3.2(mc, 1H), 4.5(s, 2H), 7.1–7.7 (m, 7H), 8.0–8.2(m, 2H) |
| v | XVIIv | N | iC₃H₇ | 4-FC₆H₄ | iC₃H₇ | 83 | 92–94 0.63$^b$ | 426, 424(M⁺+H) 1.25(d, 6H), 1.40(d, 6H), 3.4(h, 2H)4.48(S, 2H), 7.0–8.0(m, 4H) |
| w | XVIIw | N | iC₃H₇ | 4-FC₆H₄ | iC₃H₇ | 71 | oil 0.65$^b$ oil | 350(M⁺+H) — 404(M⁺+H) |

$^a$Cyclohexane/ethyl acetate 1:1
$^b$Cyclohexane/ethyl acetate 2:1
$^c$Cyclohexane/ethyl acetate 4:1
$^d$Dichloromethane/methanol 9:1
$^e$Cyclohexane/ethyl acetate 10:1

EXAMPLE 7

General procedure for the preparation of compounds of the general formula III

Example 7a (R¹=CH₃, R²=4-FC₆H₄, R³=CH₃, Z=CH, X=Br)

2,6-Dimethyl-4-(4-fluorophenyl)pyridin-3-ylmethyl-triphenylphosphonium bromide IIIa A solution of 6.4 g (22.5 mmol) of 2,6-dimethyl-4-(4-fluorophenyl)pyridin-3-ylmethyl bromide XVIIa and 6.2 g (23 mmol) of triphenylphosphine in 200 ml of toluene was refluxed for 5 h, monitoring by TLC. On cooling the reaction solution, the phosphonium salt which had formed separated out in the form of white crystals. These were filtered off with suction, washed with ether and dried in vacuo. The yield of IIIa was 11.2 g (89%).

Melting point: 218°–220° C.

¹H NMR (CDCl₃; 60 MHz): δ=2.3 (d,J=2 Hz, 3H); 2.5 (d,J=3 Hz, 3H); 6.5 (d,J=16 Hz, 2H); 6.8–7.9 (m,20H) ppm.

MS: 476 (M⁺ cation)

EXAMPLES 7b–7w

The compounds IIIb–IIIw were prepared in a manner analogous to that described in Example 7a (cf. Table 9).

TABLE 9

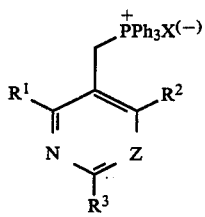

| Example | Compound | X | Z | R¹ | R² | R³ | Yield % | $R_f$ Melting point °C. | ¹H-NMR: δ/ppm = MS: m/e = |
|---|---|---|---|---|---|---|---|---|---|
| b | IIIb | Br | CH | $CH_3$ | $4-ClC_6H_4$ | $CH_3$ | 54 | 0.00[a] | 2.3(d, J=2Hz, 3H), 2.5 (d, J=3Hz, 3H), 5.5(d, J=14Hz, 2H), 6.6-8.0(m, 20H). 494, 492($M^+$ cation) |
| c | IIIc | Br | CH | $CH_3$ | $4-FC_6H_4$ | $C_6H_5$ | 93 | oil 0.02[a] | 2.4(d, J=2Hz, 3H), 5.6 (d, J=14Hz, 2H), 6.9-8.1 (m, 25H). 538($M^+$ cation) |
| d | IIId | Br | CH | $iC_3H_7$ | $4-FC_6H_4$ | $CH_3$ | 65 | 230-232 0.03[a] | 0.8(d, J=7Hz, 6H), 2.5 (d, J=3Hz, 3H), 2.8 (mc, 1H), 5.5(d, J=14Hz, 2H), 6.8-8.0(m, 20H). 504 ($M^+$ cation) |
| e | IIIe | Br | CH | $iC_3H_7$ | $4-FC_6H_4$ | $C_6H_5$ | 68 | 209 0.05[b] | 1.0 (d, J=7Hz, 6H), 3.0 (mc, 1H), 5.6(d, J=14Hz, 2H), 6.8-8.2(m, 25H) 566($M^+$ cation) |
| f | IIIf | Br | CH | $4-FC_6H_4$ | $iC_3H_7$ | $C_6H_5$ | 75 | 250 0.25[c] | 0.9(d, J=7Hz, 6H), 3.4 (mc, 1H), 5.2(d, J=14Hz, 2H), 7.0-8.2(m, 25H) 566($M^+$ cation) |
| g | IIIg | Br | CH | $t-C_4H_9$ | $4-FC_6H_4$ | $C_6H_5$ | 71 | 254 0.08[b] | 1.0(s, 9H), 5.8(d, J=14Hz, 2H), 6.8-8.2(25H) 580($M^+$ cation) |
| h | IIIh | Br | CH | $iC_3H_7$ | $4CH_3OC_6H_4$ | $C_6H_5$ | 92 | 250 0.05[b] | 1.0(d, J=7Hz, 6H), 3.0 (mc, 1H), 3.9(s, 3H), 6.5 (d, J=14Hz, 2H), 6.8-8.2 (m, 25H) 578($M^+$ cation) |
| i | IIIi | Br | CH | $iC_3H_7$ | $4-FC_6H_4$ | $2,5(CH_3)_2C_6H_3$ | 86 | 274 0.06[b] | 0.8(d, J=7Hz, 6H), 2.3(s, 6H), 3.8(h, J=7Hz, 1H), 5.0(d, J=14Hz, 2H), 7.0-7.9(m, 23H) 594($M^+$ cation) |
| j | IIIj | Br | CH | $iC_3H_7$ | $4-FC_6H_4$ | $4-FC_6H_4$ | 91 | 250 0.04[b] | 1.0(d, J=7Hz, 6H), 3.0(mc, 1H), 5.5(d, J=14Hz, 2H), 7.0-8.2(m, 24H) 584($M^+$ cation) |
| k | IIIk | Br | N | $CH_3$ | $4-FC_6H_4$ | $CH_3$ | 89 | 95-98 0.49[c] | 5.7(d, J=15Hz, 2H) 477($M^+$ cation) |
| l | IIIl | Br | N | $CH_3$ | $4-ClC_6H_4$ | $CH_3$ | 93 | 232-236 0.50[c] | 5.7(d, J=15Hz, 2H) 495, 493($M^+$ cation) |
| m | IIIm | Br | N | $CH_3$ | $cC_6H_{11}$ | $CH_3$ | 90 | 217-219 0.72[c] | 5.7(d, J=15Hz, 2H) 465($M^+$ cation) |
| n | IIIn | Br | N | $CH_3$ | $4-ClC_6H_4$ | H | 81 | >250 0.26[c] | 5.7(d, J=15Hz, 2H) 418,479($M^+$ cation) |
| o | IIIo | Br | N | $iC_3H_7$ | $4-FC_6H_4$ | $C_6H_5$ | 94 | >250 0.52[c] | 567($M^+$ cation) |
| p | IIIp | Br | N | $iC_3H_7$ | $4-FC_6H_4$ | $CH_3$ | 85 | 272-274 0.73[c] | 0.9(d, J=7Hz, 6H), 2.5 (d, J=2Hz, 3H), 2.7(mc, 1H), 5.6(d, J=14Hz, 2H), 7.0-8.3(m, 20H) 505($M^+$ cation) |
| q | IIIq | CH | Br | $iC_3H_7$ | $4-FC_6H_4$ | $iC_3H_7$ | 80 | oil 0.02[b] | 0.9(d, J=7Hz, 6H), 1.2 (d, J=7Hz,6H), 2.6-3.2 (m, 2H), 5.4(d, J=16Hz, 2H), 6.7-7.9(m, 20H), 532($M^+$ cation) |
| r | IIIr | CH | Br | $iC_3H_7$ | $4-FC_6H_4$ | $tC_4H_9$ | 74 | 110(decomp.) — | 0.9(d, J=7Hz, 6H), 1.3 (s, 9H), 2.9(mc, 1H), 5.5 (d, J=14Hz, 2H), 6.8-7.9 (m, 20H) 546($M^+$ cation) |
| s | IIIs | CH | Br | $iC_3H_7$ | $4-FC_6H_4$ | $cC_6H_{11}$ | 98 | >100(decomp.) — | 0.9(d, J=7Hz, 6H), 1.4-2.0 (m, 10H), 2.2-3.0(m, 2H), 5.5(d, J=14Hz, 2H), 6.8-7.6(m, 20H) |

TABLE 9-continued

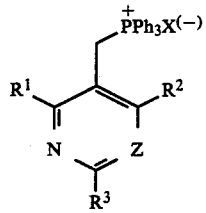

| Example | Compound | X | Z | $R^1$ | $R^2$ | $R^3$ | Yield % | Melting point °C. | $R_f$ / $^1$H-NMR: δ/ppm = MS: m/e = |
|---|---|---|---|---|---|---|---|---|---|
| t | IIIt | CH | Br | $C_2H_5$ | $4\text{-}FC_6H_4$ | $C_6H_5$ | 94 | 223–226(decomp.) — | 572($M^+$ cation) 1.1(t, J=7Hz, 3H), 2.6 (q, J=7Hz, 2H), 5.5(d, J=14Hz, 2H), 6.9–8.2(m, 25H) |
| u | IIIu | CH | Br | $cC_6H_{11}$ | $4\text{-}FC_6H_4$ | $C_6H_5$ | 97 | 218–220 — | 594($M^+$ cation) 0.8–2.0(m, 11H), 2.5(mc, 1H), 5.5(d, J=16Hz, 2H), 7.0–8.2(m, 25H) |
| v | IIIv | N | Br | $iC_3H_7$ | $4\text{-}FC_6H_4$ | $iC_3H_7$ | 59 | >270(decomp.) — | 606($M^+$ cation) 0.95(d, 6H), 1.4(d, 6H), 3.15(h, 2H), 5.8(d, J=16Hz, 2H), 7.0–8.0(m, 19H) |
| w | IIIw | N | Br | $iC_3H_7$ | $4\text{-}FC_6H_4$ | $4\text{-}FC_6H_4$ | 78 | >250(decomp.) — 248–255 | 533($M^+$ cation) 1.0(d, 6H), 3.0(h, 1H), 5.6(d, J=16Hz, 2H), 7.0–8.8(m, 23H) |

$^a$Cyclohexane/ethyl acetate 1:1
$^b$Cyclohexane/ethyl acetate 2:1
$^c$Dichloromethane/methanol 9:1

EXAMPLE 8

General procedure for the preparation of compounds of the general formula V

Example 8a ($R^1$=$CH_3$, $R^2$=$4\text{-}FC_6H_4$, $R^3$=$CH_3$, A—B=—CH=CH—)

(4R,6S)-4-(tert.Butyldiphenylsilyloxy)-6-(2-(2,6-dimethyl-4-(4-fluorophenyl)pyridin-3-yl)ethenyl)-2-methoxy-3,4,5,6-tetrahydropyranones Z-Va and E-Va 12.0 ml (19.2 mmol) of a 1.6-molar solution of n-butyllithium in hexane was added dropwise, at 0° C., to a solution of 9.70 g (17.5 mmol) of 2,6-dimethyl-4-(4-fluorophenyl)pyridin-3-ylmethyltriphenylphosphonium bromide IIIa in 100 ml of THF. The mixture was stirred at room temperature for 30 min, and then a solution of 7.29 g (18.4 mmol) of the aldehyde IV in 40 ml of THF was added dropwise. After the mixture had been stirred for one hour it was quenched by addition of water, the pH was adjusted to between 5 and 6 with acetic acid, and the mixture was extracted several times with ether. The combined organic extracts were washed with saturated sodium bicarbonate solution and water, dried over magnesium sulfate and evaporated. The remaining crude mixture of diastereomers was fractionated by column chromatography (silica gel, cyclohexane-ethyl acetate 2:1).

Yield: 2.36 g of Z-Va and 4.99 g of E-Va, corresponding to 70% with a Z:E ratio of 32:68 (about 1:2).

Z-Va: melting point: 111°–113° C.

$^1$H NMR: ε/ppm=0.9 (s,9H), 1.0–1.8 (m,4H), 2.6 (s,6H), 3.3 (s,3H), 4.2 (mc,1H), 4.3 (mc,1H), 5.5 (mc,1H), 6.3 (d, J=10 Hz,1H), 6.9–7.8 (m,15H).

MS: m/e=596 ($M^+$+H).

E-VA: melting point: oil.

$^1$H NMR: ε/ppm=1.1 (s,9H), 1.1–1.9 (m,4H), 2.5 (s,3H), 2.6 (s,3H), 3.5 (s,3H), 4.2 (mc,1H), 4.5 (mc,1H), 4.9 (mc,1H), 5.5 (dd, J=16 Hz,6 Hz, 1H), 6.43 (d,J=16 Hz,1H), 6.9–7.7 (m,15H).

MS: m/e=596 ($M^+$+H).

EXAMPLES 8b–8w

The compounds Vb–Vw were prepared in a manner analogous to that described in Example 8a (cf. Table 10)

TABLE 10

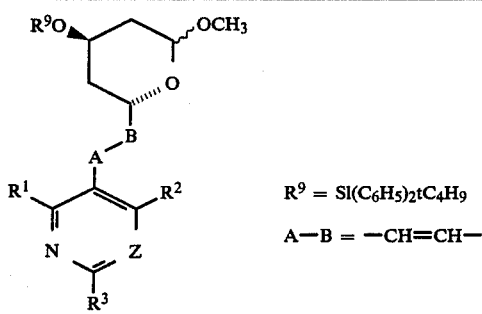

$R^9 = Si(C_6H_5)_2tC_4H_9$ $A-B = -CH=CH-$

| Example | Compound | Z | $R^1$ | $R^2$ | $R^3$ | Yield % Z:E | $R_f$ Melting point °C.(Z;E) | $^1$H NMR: δ/ppm = MS:m/e = |
|---|---|---|---|---|---|---|---|---|
| b | Vb | CH | $CH_3$ | $4-ClC_6H_4$ | $CH_3$ | 75  1:2 | 0.34;0.24[a]  oil,oil | Z:0.9(s, 9H), 1.0-1.8 (m, 4H), 2.6(s, 6H), 3.3 (s, 3H), 4.2(mc, 1H), 4.3 (mc, 1H), 4.5(mc, 1H), 5.5 (mc, 1H), 6.3(d, J=10Hz, 1H), 8.9-7.7(m, 15H), E:1.1(s.9H), 1.1-1.9(m, 4H), 2.5(s.3H), 2.6(s, 3H), 3.5(s, 3H), 4.3(mc, 1H), 4.5(mc, 1H), 4.9(mc, 1H), 5.5(mc, 1H), 6.5(d, J= 16Hz, 1H), 6.9-7.6(m, 15H).  613, 611(M$^+$) |
| c | Vc | CH | $CH_3$ | $4-FC_6H_4$ | $C_6H_5$ | 71  1:1.5 | 0.60;0.53[b]  oil;oil | 657(M$^+$) |
| d | Vd | CH | $iC_3H_7$ | $4-FC_6H_4$ | $CH_3$ | 68  1:2 | 0.45;0.42[c]  oil;oil | Z:0.9(s.9H), 1.0-1.9 (m, 10H), 2.6(s, 3H), 3.2-3.3(m, 4H), 4.2(mc, 1H), 4.3(mc, 1H), 4.5(mc, 1H), 5.3(mc, 1H), 6.3(d, J= 10Hz, 1H), 6.9-7.7(m, 15H), E:1.1(s,9H), 1.2-1.9(m, 10H), 2.5(s, 3H), 3.4(mc, 1H), 3.5(s, 3H), 4.2(mc, 1H), 5.3(mc, 1H), 6.5(d, J=16Hz, 1H), 6.9-7.7(m, 15H).  623(M$^+$) |
| e | Ve | CH | $iC_3H_7$ | $4-FC_6H_4$ | $C_6H_5$ | 74  <1:>20 | —;0.89[a] | E:1.1(s, 9H), 1.3-1.9 (m, 10H), 3.4-3.5(m, 4H), 4.3 (mc, 1H), 4.9 (mc, 1H), 6.5(d, J=16Hz, 1H), 7.0 (mc, 2H), 7.2(mc, 2H), 7.2-7.7(m, 12H), 8.1(mc, 4H)  685(M$^+$) |
| f | Vf | CH | $4-FC_6H_4$ | $iC_3H_7$ | $C_6H_5$ | <1:>20 | —;oil  —;0.62[d] | 685(M$^+$) |
| g | Vg | CH | $tC_4H_9$ | $4-FC_6H_4$ | $C_6H_5$ | <1:>20 | —, 0.70[d]  —, oil | 699(M$^+$) |
| h | Vh | CH | $iC_3H_7$ | $4-CH_3OC_6H_4$ | $C_6H_5$ | 69  <1:>20 | —;0.64[d]  —;oil | 690(M$^+$+H) |
| i | Vi | CH | $iC_3H_7$ | $4-FC_6H_4$ | $2,5-(CH_3)_2C_6H_3$ | 72 | —, 0.77[d] | 1.1(s, 9H), 1.2-1.4(m, 9H), 1.9(mc, 1H), 2.4(s, 3H), 2.5(s, 3H), 3.4(h, J=7Hz, 1H), 3.5(s, 3H), 4.3(mc, 1H), 4.5(mc, 1H) 4.9(mc, 1H), 5.4(mc, 1H) 6.6(d, J=16Hz, 1H), 7.0-7.5(m, 14H), 7.7(mc, 4H)  714(M$^+$+H) |
| j | Vj | CH | $iC_3H_7$ | $4-FC_6H_4$ | $iC_3H_7$ | <1:>20  76  <1:>20 | —;0.56[d]  —;oil | 704(M$^+$+H) |
| k | Vk | N | $CH_3$ | $4-FC_6H_4$ | $CH_3$ | 71  1:1 | 0.38;0.35[d]  oil;oil | E:1.1(s, 9H), 1.1-1.9(m, 4H), 2.6(s, 3H), 2.7(s, 3H), 3.5(s, 3H), 4.3(me, 1H), 4.9 (mc, 1H), 5.6(mc, 1H), 6.5(d, J=16Hz, 1H), 7.1(mc, 2H), 7.3-7.8(m, 12H).  597(M$^+$+H) |
| l | Vl | N | $CH_3$ | $4-ClC_6H_4$ | $CH_3$ | 69  1:1 | 0.41;0.37[d]  oil;oil | E: 1.1(s, 9H), 1.2-1.9(m, 4H), 2.6(s, 3H), 2.7(s, 3H), 3.5(s, 3H), 4.3-4.4 (m, 1H), 4.5-4.6(m, 1H), 4.9(mc, 1H), 5.6(mc, 1H), 6.5(d, J=16Hz, 1H), 7.3-7.7 (m, 14H). |

TABLE 10-continued

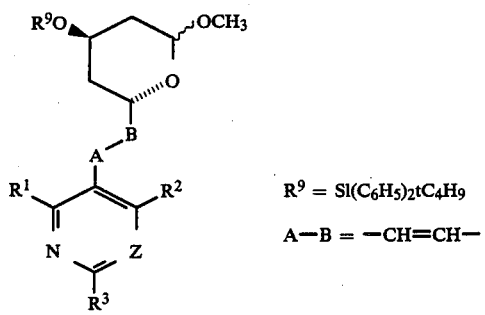

$R^9 = Sl(C_6H_5)_2tC_4H_9$ $A{-}B = {-}CH{=}CH{-}$

| Example | Compound | Z | $R^1$ | $R^2$ | $R^3$ | Yield % Z:E | $R_f$ Melting point °C.(Z;E) | $^1H$ NMR: δ/ppm = MS:m/e = |
|---|---|---|---|---|---|---|---|---|
| m | Vm | N | $CH_3$ | $cC_6H_{11}$ | $CH_3$ | 72 1:1 | 0.42;0.39[d] oil;oil | 614, 612(M+) |
| n | Vn | N | $CH_3$ | $4\text{-}ClC_6H_4$ | H | 94 1:1 | 0.39;0.36[d] | 584(M+) |
| o | Vo | N | $iC_3H_7$ | $4\text{-}FC_6H_4$ | $C_6H_5$ | 73 2:1 | 0.27;0.44[d] | 600, 598(M+) E:1.1(s, 9H), 1.1–1.9 (m, 10H), 3.4(h, J=7Hz, 1H), 3.5(s, 3H), 4.3(mc, 1H), 4.9(mc, 1H), 5.6 (mc, 1H), 6.6(dd, J=16Hz, 1Hz, 1H), 7.1–7.8(m, 17H), 8.5–8.6(m, 2H) |
| p | Vp | N | $iC_3H_7$ | $4\text{-}FC_6H_4$ | $CH_3$ | 91 1:1 | 0.42;0.40[d] | |
| q | Vq | CH | $iC_3H_7$ | $4\text{-}FC_6H_4$ | $iC_3H_7$ | 62 | —;0.88[b] | 624(M+) 1.1(s, 9H), 1.2–1.8(m, 16H), 3.0(h, J=7Hz, 1H), 3.4(h, J=Hz, 1H), 3.5(s, 3H), 4.2(mc, 1H), 4.5(mc, 1H), 4.9(mc, 1H), 5.3(mc, 1H), 6.5(dd, J=16Hz, 2Hz, 1H), 6.9–7.7(m, 15H) |
| r | Vr | CH | $iC_3H_7$ | $4\text{-}FC_6H_4$ | $tC_4H_9$ | <1:>20 84 | —;oil —;0.58[e] | 1.1(s, 9H), 1.3(mc, 6H), 1.4(s, 9H). 1.5–1.9(m, 4H), 3.4(h, J=7Hz, 1H), 3.5(s, 3H), 4.2(mc, 1H), 4.5(mc, 1H), 4.9(mc, 1H), 5.4(dd, J=16Hz, 6Hz, 1H), 6.5(dd, J=16Hz, 1Hz, 1H), 6.9–7.7 (m, 15H) |
| s | Vs | CH | $iC_3H_7$ | $4\text{-}FC_6H_4$ | $cC_6H_{11}$ | <1:>20 49 | —;oil —;0.40[f] | 666(M++H) 1.1(s, 9H), 1.3(mc, 6H), 1.4–2.0(m, 14H), 2.7(mc, 1H), 3.3(h, J=7Hz, 1H), 3.5(s, 3H), 4.2(mc, 1H), 4.5(mc, 1H), 5.3(mc, 1H), 6.5(d, J=16Hz, 1H), 6.7–7.7 (m, 15H) |
| t | Vt | CH | $C_2H_5$ | $4\text{-}FC_6H_4$ | $C_6H_5$ | <1:>20 45 65:35 | —;oil 0.53;0.53[b] oil;oil | 692(M++H) — |
| u | Vu | CH | $cC_6H_{11}$ | $4\text{-}FC_6H_4$ | $C_6H_5$ | 50 | —;0.50[b] | 672(M++H) t: 1.1(s, 9H), 1.3–2.0(m, 14H), 3.5(s, 3H), 4.2(mc, 1H), 4.5(mc, 1H), 5.4(mc, 1H), 6.5(dd, J=16Hz, 1Hz, 1H), 7.0–7.5(m, 12H), 8.0–8.2(m, 3H) |
| v | Vv | N | $iC_3H_7$ | $4\text{-}FC_6H_4$ | $iC_3H_7$ | 89 | —;oil —;0.70[a] | 726(M++H) 3.5(s, 3H), 6.5(dd, J=16Hz, 1H) |
| w | Vw | N | $iC_3H_7$ | $4\text{-}FC_6H_4$ | $4\text{-}FC_6H_4$ | 67 | —;oil —;64[a] —;oil | 653(M++H) 705(M++H) |

[a] Cyclohexane/ethyl acetate 2:1
[b] Cyclohexane/ethyl acetate 4:1
[c] Cyclohexane/ethyl acetate 8:1
[d] Cyclohexane/ethyl acetate 1:1
[e] Cyclohexane/ethyl acetate 10:1
[f] Cyclohexane/ethyl acetate 30:1

EXAMPLE 9

General procedure for the preparation of compounds of the general formula VI

Example 9a ($R^1$=$CH_3$, $R^2$=4-$FC_6H_4$, $R^3$=$CH_3$, A—B=—CH=CH—)

(4R,6S)-4-(tert.Butyldiphenylsilyloxy)-6-(2-(2,6-dimethyl-4-(4-fluorophenyl)pyridin-3-yl)ethenyl)-2-hydroxy-3,4,5,6-tetrahydro-2H-pyrans Z-VIa and E-VIa 7.25 g (12.4 mmol) of a 32:68 mixture of the compounds Z-Va and E-Va were boiled under reflux in a mixed solvent composed of 85 ml of THF, 85 ml of water and 140 ml of glacial acetic acid for 48 h. 200 ml of toluene were added, and then the reaction solution was evaporated. Residues of acetic acid were removed from the residue by adding toluene and evaporating several times, then the residue was taken up in ether, and the solution was shaken with saturated sodium bicarbonate solution, dried over magnesium sulfate and again evaporated. Subsequent purification by chromatography provided 1.35 g of Z-VIa and 3.14 g of E-VIa, corresponding to a yield of 63% and Z:E ratio of 30:70.

Z-VIa M.p.: 147°–149° C.

$^1$H-NMR: δ/ppm=0.9 (s,9H), 1.0–1.9 (m,4H), 2.5 (s,6H), 4.0–4.4 (m,2H), 4.8–6.5 (m,3H), 6.9–7.6 (m,15H).

MS: m/e=581 (M+).

E-VIa: M.p.: 119° C.

$^1$H-NMR: δ/ppm=1.1 (s,9H), 1.2–2.0 (m,4H), 2.5 (s,3H), 2.6 (s,3H), 3.9–5.0 (m,3H), 5.1–5.6 (m,2H), 6.4 (d,J=16 Hz,1H), 6.9–7.8 (m,15H).

Ms: m/e=581 (M+).

EXAMPLES 9b–9w

The compounds VIb–VIw were prepared in a manner analogous to that described in Example 9a (cf. Table 11)

TABLE 11

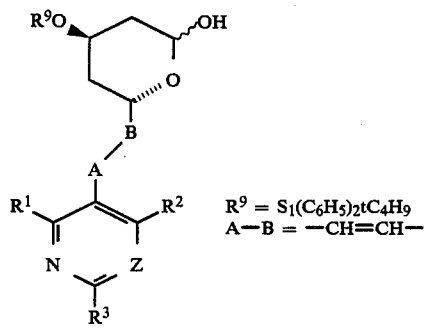

$R^9$ = $S_1(C_6H_5)_2tC_4H_9$
A—B = —CH=CH—

| Example | Compound | Z | $R^1$ | $R^2$ | $R^3$ | Yield % | $R_f$(Z;E) Melting(Z;E) point °C. | $^1$H NMR: δ/ppm = MS : m/e = |
|---|---|---|---|---|---|---|---|---|
| b | VIb | CH | $CH_3$ | 4-$ClC_6H_4$ | $CH_3$ | 82 | 0.37; 0.29$^a$ | 600,598 (M+ +H) |
| b | VIb | CH | $CH_3$ | 4-$ClC_6H_4$ | $CH_3$ | 82 | —; 98 | 600,598 (M+ +H) |
| c | VIc | CH | $CH_3$ | 4-$FC_6H_4$ | $C_6H_5$ | 61 | 0.15; 0.15$^b$ oil; oil | 644 (M+ +H) |
| d | VId | CH | $iC_3H_7$ | 4-$FC_6H_4$ | $CH_3$ | 82 | 0.77; 0.72$^a$ oil; oil | 610 (M+ +H) |
| e | VIe | CH | $iC_3H_7$ | 4-$FC_6H_4$ | $C_6H_5$ | 74 | —; 0.32$^c$ —; oil | E: 1.1–1.8 (m, 19H), 3.4 (h, J=7Hz,1H), 4.3 (mc, 1H), 4.9 (mc, 1H), 5.2–5.6 (m, 3H), 6.5 (mc, 1H), 6.9–8.2 (m, 20H). 671 (M+) |
| f | VIf | CH | 4-$FC_6H_4$ | $iC_3H_7$ | $C_6H_5$ | 84 | —; 0.25$^b$ —; oil | 671 (M+) |
| g | VIg | CH | $tC_4H_9$ | 4-$FC_6H_4$ | $C_6H_5$ | 71 | —; 0.40$^c$ —; oil | 685 (M+) |
| h | VIh | CH | $iC_3H_7$ | 4-$CH_3OC_6H_4$ | $C_6H_5$ | 65 | —; 0.37$^c$ —; oil | 683 (M+) |
| i | VIi | CH | $iC_3H_7$ | 4-$FC_6H_4$ | 2,5-$(CH_3)_2C_6H_3$ | 69 | —; 0.47$^c$ —; oil | 699 (M+) |
| j | VIj | CH | $iC_3H_7$ | 4-$FC_6H_4$ | 4-$FC_6H_4$ | 75 | —; 0.35$^c$ —; oil | 705 (M+) |
| k | VIk | N | $CH_3$ | 4-$FC_6H_4$ | $CH_3$ | 97 | 0.18; 0.13$^a$ oil; oil | E: 2.6 (s,3H), 2.7, (s,3H), 5.6 (mc, 1H) 6.5 (dd, J=16Hz, 1Hz, 1H) 598 (M+) |
| l | VII | N | $CH_3$ | 4-$ClC_6H_4$ | $CH_3$ | 68 | 0.21; 0.15$^a$ oil; oil | E: 2.5(s,3H), 2.7 (s, 3H), 5.6 (mc, 1H), 6.4(dd, J=16Hz, 1Hz). 586,584 M+ |
| m | VIm | N | $CH_3$ | $cC_6H_{11}$ | $CH_3$ | 72 | 0.20; 0.17$^a$ oil; oil | 570 (M+) |
| n | VIn | N | $CH_3$ | 4-$ClC_6H_4$ | H | 78 | 0.22; 0.18$^a$ | 586,584 (M+) |
| o | VIo | N | $iC_3H_7$ | 4-$FC_6H_4$ | $C_6H_5$ | 84 | 0.17; 0.15$^a$ oil; oil | E: 1.1 (s,9H), 1.2–2.6(m,4H), 3.5 |

TABLE 11-continued

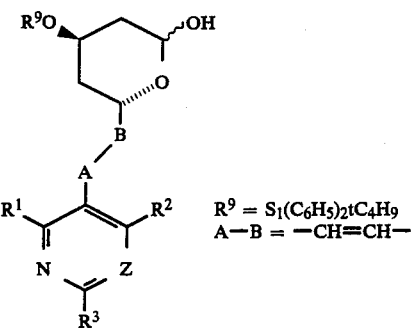

$R^9 = S_1(C_6H_5)_2tC_4H_9$
$A—B = —CH=CH—$

| Example | Compound | Z | $R^1$ | $R^2$ | $R^3$ | Yield % | $R_f$(Z;E) Melting(Z;E) point °C | $^1$H NMR: δ/ppm = MS : m/e = |
|---|---|---|---|---|---|---|---|---|
| | | | | | | | | (h, J=7Hz, 1H), 4.3 (mc, 1H), 4.9(mc, 1H), 5.5(mc, 1H), 6.5(d, J=16Hz, 1H), 6.9–8.6(m, 19H), 673 (M$^+$+H) |
| p | VIp | N | iC$_3$H$_7$ | 4-FC$_6$H$_4$ | —CH$_3$ | 86 | —; 0.13$^a$ —; oil | 610(M$^+$) |
| q | VIq | CH | iC$_3$H$_7$ | 4-FC$_6$H$_4$ | iC$_3$H$_7$ | 50 | —; 0.55$^b$ —; oil | — 638 (M$^+$+H) |
| r | VIr | CH | iC$_3$H$_7$ | 4-FC$_6$H$_4$ | tC$_4$H$_9$ | 54 | —; 0.54$^d$ —; oil | — 652 (M$^+$+H) |
| s | VIs | CH | iC$_3$H$_7$ | 4-FC$_6$H$_4$ | cC$_6$H$_{11}$ | 48 | —; 0.41$^d$ —; oil | — 678 (M$^+$+H) |
| t | VIt | CH | C$_2$H$_5$ | 4-FC$_6$H$_4$ | C$_6$H$_5$ | 71 | 0.25; 0.25$^b$ oil; oil | — 658 (M$^+$+H) |
| u | VIu | CH | cC$_6$H$_{11}$ | 4-FC$_6$H$_4$ | C$_6$H$_5$ | 54 | —; 0.33 (4:1) —; oil | — 712 (M$^+$+H) |
| v | VIv | N | iC$_3$H$_7$ | 4-FC$_6$H$_4$ | iC$_3$H$_7$ | 100 | —; 0.54$^e$ —; oil | — 639 (M$^+$+H) |
| w | VIw | N | iC$_3$H$_7$ | 4-FC$_6$H$_4$ | 4-FC$_6$H$_4$ | 98 | —; 0.30$^e$ —; oil | — 691 (M$^+$+H) |

$^a$Cyclohexane/ethyl acetate 1:1
$^b$Cyclohexane/ethyl acetate 4:1
$^c$Cyclohexane/ethyl acetate 5:1
$^d$Cyclohexane/ethyl acetate 10:1
$^e$Cyclohexane/ethyl acetate 2:1

EXAMPLE 10

General procedure for the preparation of the compounds of the general formula VII Example 10a ($R^1$=CH$_3$, $R^2$=4-FC$_6$H$_4$, $R^3$=CH$_3$, AB=—CH=CH—)

(4R,6S)-4-(tert,Butyldiphenylsilyloxy)-6-(2-(2,6-dimethyl-4-(4-fluorophenyl)pyridin-3-yl)ethenyl)-3,4,5,6-tetrahydro-2H-pyran-2-ones Z-VIIa and E-VIIa 4.30 g (7.4 mmol) of a 30:70 mixture of the compounds Z-VIa and E-VIa dissolved in 20 ml of dichloromethane were added dropwise to a solution of 8.32 g (37.0 mmol) of N-iodosuccinimide and 2.73 g (7.4 mmol) of tetra-n-butylammonium iodide in 100 ml of dichloromethane. The mixture was stirred at room temperature for 2H and then added to water, and the mixture was extracted with ether several times. The combined exracts were decolorized with sodium thiosulfate solution, washed with water, dried over magnesium sulfate and evaporated. The residue was taken up in diisopropyl ether, the solution was filtered, and the filtrate was again evaporated. Purification of the remaining oil by column chromatography (silica gel, deactivated with 10% water; cyclohexane/ethyl acetate 1:1) resulted in 0.82 g of Z-VIIa and 2.45 g of E-VIIa. This corresponds to a yield of 76% with a Z:E ratio of 25:75.

Z-VIIa: melting point: 188° C.

$^1$H-NMR: δ/ppm=0.9 (s,9H), 1.3–1.7 (m,4H), 2.4 (mc,2H), 2.6 (s,6H), 4.2 (mc,1H), 5.0 (mc,1H), 5.6 (mc,1H), 6.5 (d,J=11 Hz,1H), 6.9–7.5 (m,15H).

MS: m/e=580 (M$^+$+H).

E-VIIa: melting point: oil.

$^1$H-NMR: δ/ppm=1.1 (s,9H), 1.3–1.7 (m,2H), 2.4–2.6 (m,8H), 4.2 (mc,1H), 5.2 (mc,1H), 5.4 (mc,1H), 6.5 (d,J=16 Hz,1H), 6.9–7.7 (m,15H).

MS: m/e=580 (M$^+$+H).

EXAMPLES 10b–10w

The compounds VIIb–VIIw were prepared in a manner analogous to that described in Example 10a (cf. Table 12)

TABLE 12

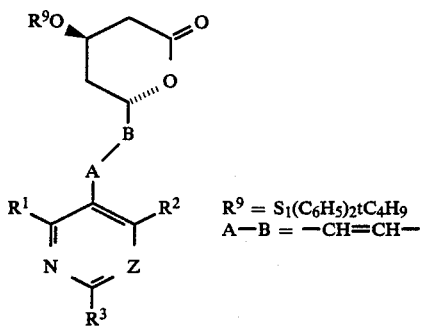

$R^9 = S_1(C_6H_5)_2tC_4H_9$
$A-B = -CH=CH-$

| Example | Compound | Z | $R^1$ | $R^2$ | $R^3$ | Yield % | $R_f$(Z;E) Melting(Z;E) point °C. | $^1$H NMR: δ/ppm = MS : m/e = |
|---|---|---|---|---|---|---|---|---|
| b | VIIb | CH | $CH_3$ | 4-$ClC_6H_4$ | $CH_3$ | 57 | 0.48; 0.39$^a$ oil; oil | Z: 1.0(s,9H), 1.4–1.7(m, 4H), 2.4 (mc, 2H), 2.6(s, 6H), 4.2(mc, 1H), 5.0 (mc, 1H), 5.6(mc, 1H) 6.5(d, J =11Hz, 1H), 6.9–7.5 (m, 15H). E: 1.1(s, 9H), 1.4–1.8(m, 4H), 2.4–2.7 (m,8H), 4.3(mc, 1H), 5.2(mc, 1H), 5.4(mc, 1H), 6.5 (d, J = 16Hz, 1H), 6.9-7.6 (m, 15H). 597, 595 (M$^+$) |
| c | VIIc | CH | $CH_3$ | 4-$FC_6H_4$ | $C_6H_5$ | 66 | 0.41; 0.35$^b$ oil; oil | 655 (M$^+$) |
| d | VIId | CH | $iC_3H_7$ | 4-$FC_6H_4$ | $CH_3$ | 89 | 0.81; 0.77$^c$ oil; oil | 607 (M$^+$) |
| e | VIIe | CH | $iC_3H_7$ | 4-$FC_6H_4$ | $C_6H_5$ | 70 | —; 0.51$^b$ oil;oil | E: 1.1(s, 9H), 1.2–1.8(m, 10H), 3.4 (d, J=7Hz, 1H), 4.3(mc, 1H), 5.2–5.4(m, 2H), 6.5 (d, J = 16Hz, 1H), 7.0–8.1(m, 20H) 669(M$^+$) |
| f | VIIf | CH | 4-$FC_6H_4$ | $iC_3H_7$ | $C_6H_5$ | 76 | —; 0.36$^b$ —; oil | 669 (M$^+$) |
| g | VIIg | CH | $tC_4H_9$ | 4-$FC_6H_4$ | $C_6H_5$ | 83 | —; 0.45$^b$ —; oil | 683 (M$^+$) |
| h | VIIh | CH | $iC_3H_7$ | 4-$CH_3OC_6H_4$ | $C_6H_5$ | 88 | —; 0.55$^b$ —; oil | 681 (M$^+$) |
| i | VIIi | CH | $iC_3H_7$ | 4-$FC_6H_4$ | 2,5-$(CH_3)_2C_6H_3$ | 79 | —; 0.60$^b$ —; oil | 697 (M$^+$) |
| j | VIIj | CH | $iC_3H_7$ | 4-$FC_6H_4$ | 4-$FC_6H_4$ | 65 | —; 0.54$^d$ —; oil | 687 (M$^+$) |
| k | VIIk | N | $CH_3$ | 4-$FC_6H_4$ | $CH_3$ | 64 | 0.40; 0.37$^a$ oil; oil | E: 1.1 (s,9H), 1.3–2.6 (m,4H), 2.6 (s,3H), 2.7 (s,3H), 4.2–4.3 (m,1H), 5.2–5.4 (m,1H), 5.6 (mc,1H), 6.6 (d,J = 16Hz,1H), 7.0–7.7 (m,14H). |
| l | VIIl | N | $CH_3$ | 4-$ClC_6H_4$ | $CH_3$ | 95 | 0.25; 0.23$^a$ oil; oil | E: 2.5 (s,3H), 2.7 (s,3H), 4.2–4.3 (m,1H), 5.2–5.4 (m,1H), 5.6 (mc,1H), 6.6 (mc, 1H), 7.0–7.7 (m,14H). |
| m | VIIm | N | $CH_3$ | $cC_6H_{11}$ | $CH_3$ | 72 | 0.41; 0.35$^a$ oil; oil | 568 (M$^+$) |
| n | VIIn | N | $CH_3$ | 4-$ClC_6H_4$ | H | 84 | 0.30; 0.27$^a$ | 582 (M$^+$) |
| o | VIIo | N | $iC_3H_7$ | 4-$FC_6H_4$ | $C_6H_5$ | 93 | 0.39; 0.35$^a$ oil; oil | 4.3 (mc,1H), 5.3 (mc,1H), 5.5 (mc, 1H), 6.7 (d,J = 16Hz,1H), 7.0–7.7 |

TABLE 12-continued

[Structure: R⁹O-substituted tetrahydropyran-2-one with side chain containing A=B group, R¹, R², N, Z, R³ substituents]

$R^9 = Si(C_6H_5)_2tC_4H_9$
A—B = —CH=CH—

| Example | Compound | Z | R¹ | R² | R³ | Yield % | $R_f$(Z;E) Melting(Z;E) point °C. | ¹H NMR: δ/ppm = MS: m/e = |
|---|---|---|---|---|---|---|---|---|
| | | | | | | | | (m,7H), 8.5–8.6 (m,2H) 656 (M⁺) |
| p | VIIp | N | iC₃H₇ | 4-FC₆H₄ | CH₃ | 72 | —; 0.29[a]<br>—; oil | 608 (M⁺) |
| q | VIIq | CH | iC₃H₇ | 4-FC₆H₄ | iC₃H₇ | 87 | —; 0.32[f]<br>—; oil | —<br>636 (M⁺ + H) |
| r | VIIr | CH | iC₃H₇ | 4-FC₆H₄ | tC₄H₉ | 83 | —; 0.62[f]<br>—; oil | 1.1 (s,9H), 1.3 (mc,6H), 1.4 (s, 9H), 1.5–1.8 (m, 2H), 2.4 (mc,1H), 2.6 (mc,1H), 3.3 (mc,1H), 4.2 (mc, 1H), 5.2–5.3 (m, 2H), 6.6 (d, J = 16Hz,1H) 7.0–7.7 (m,15H) 650 (M⁺ + H) |
| s | VIIs | CH | iC₃H₇ | 4-FC₆H₄ | cC₆H₁₁ | 93 | —; 0.56[f]<br>—; 90–92 | —<br>676 (M⁺ + H) |
| t | VIIt | CH | C₂H₅ | 4-FC₆H₄ | C₆H₅ | 79 | 0.28; 0.28[e]<br>—; | —<br>656 (M⁺ + H) |
| u | VIIu | CH | cC₆H₁₁ | 4-FC₆H₄ | C₆H₅ | 91 | —; 0.41[e]<br>—; oil | 1.1 (s,9H), 1.3–1.9 (m,12H), 2.5 (mc,1H), 2.6 (mc, 1H), 3.0 (mc,1H), 4.2 (mc,1H), 5.2–5.4 (m,2H), 6.6 (d, J = 16Hz, 1H), 7.0 (mc,2H), 7.2–7.7 (m,21H), 8.1 (mc,2H) 709 (M⁺) |
| v | VIIv | N | iC₃H₇ | 4-FC₆H₄ | iC₃H₇ | 88 | —; 0,37[e]<br>—; oil | 1.1 (s,9H), 1.25 (d,6H), 1.48 (d, 6H), 1.5–1.9 (m, 2H), 2.1–2.7 (m, 2H), 3.15–3.35 (m, 2H), 4.25 (m,1H), 5.25 (m,1H), 5.4 (dd,1H), 6.6 (d, 1H), 7.0 (t,1H), 7.35–7.6 (m,14H) 636 (M⁺ + H) |
| w | VIIw | N | iC₃H₇ | 4-FC₆H₄ | 4-FC₆H₄ | 97 | —; 0.35[e]<br>—; oil | —<br>689 (M⁺ + H) |

[a]Cyclohexane/ethyl acetate 1:1
[b]Cyclohexane/ethyl acetate 3:1
[c]Cyclohexane/ethyl acetate 2:1
[d]Cyclohexane/ethyl acetate 20:1
[e]Cyclohexane/ethyl acetate 4:1
[f]Cyclohexane/ethyl acetate 10:1

EXAMPLE 11

General procedure for the preparation of compounds of the general formula I

Example 11a (R¹=CH₃, R²=4-FC₆H₄, R³=CH₃, A—B=—CH=CH—) (4R, 6S)-6-(2-(2,6-Dimethyl-4-(4-fluorophenyl)pyridin-3-yl)ethenyl)-4-hydroxy-3,4,5,6-tetrahydro-2H-pyran-2-ones Z-Ia and E-Ia A solution of 3.00 g (5.2 mmol) of a mixture of the compounds Z-VIIa and E-VIIa, 4.90 g (15.5 mmol) of tetra-n-butylammonium fluoride trihydrate and 11.8 ml (20.7 mmol) of acetic acid in 50 ml of tetrahydrofuran was stirred at room temperature for 15 h. The mixture was then added to saturated sodium bicarbonate solution, and the mixture was extracted with ether several times. The combined organic extracts were washed with saturated solution of NaCl, dried over magnesium sulfate and evaporated. The remaining product was chromatographed (silica gel, deactivated with 10% water, ethyl acetate/methanol 10:1). 0.29 g of the Z-isomers Z-Ia and 0.97 g of E-Ia were obtained, equivalent to a yield of 71% with a ratio of diastereomers (Z:E) of 23:77).

Z-Ia: melting point: 188° C.

$^1$H-NMR: δ/ppm=1.5 (mc,1H), 1.8–2.2 (m,2H), 2.4–2.6 (m,8H), 4.2 (mc,1H), 4.8 (mc,1H), 5.6 (mc,1H), 6.5 (mc,1H), 6.9 (s,1H), 7.0–7.4 (m,4H).

MS: m/e=341 (M+).

E-Ia: melting point: 205° C.

$^1$H-NMR: δ/ppm=1.6–1.9 (m,3H), 2.5 (s,3H), 2.6 (s,3H), 2.6–2.8 (m,2H), 4.3 (mc,1H), 5.3 (mc,1H), 5.5 (mc,1H), 6.6 (d,J=16 Hz,1H), 6.9 (s,1H), 7.0–7.3 (m,4H).

MS: m/e=341 (M+).

EXAMPLES 11b–11w

The compounds Ib–Iw were prepared in a manner analogous to that described in Example 11a (cf. Table 13).

TABLE 13

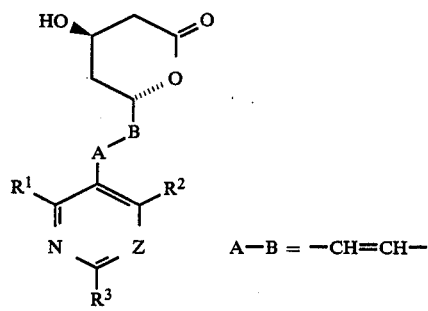

A—B = —CH=CH—

| Example | Compound | Z | R$^1$ | R$^2$ | R$^3$ | Yield % | R$_f$(Z; E) melting point °C. (Z; E) [α]$_D^{25}$(Z; E) | $^1$H NMR: δ/ppm = MS: m/e = |
|---|---|---|---|---|---|---|---|---|
| b | Ib | CH | CH$_3$ | 4-ClC$_6$H$_4$ | CH$_3$ | 65 | 0.37; 0.32$^a$ oil; oil —; — | Z: 1.5–2.1(m,3H), 2.4–2.7 (m,8H), 4.2 (mc,1H), 4.8 (mc,1H), 5.5 (mc,1H), 6.6 (d,J=10Hz,1H), 7.0 (s,1H), 7.3 (mc,1H), E: 1.6–1.8 (m,2H), 2.3–2.7 (m,8H), 4.1 (mc,1H), 5.1 (mc,1H), 5.2 (d,J=3Hz,1H), 5.5 (mc,1H), 6.5 (d,J=16Hz,1H), 7.0 (s,1H), 7.4 (mc,1H), 359,357 (M+) |
| c | Ic | CH | CH$_3$ | 4-FC$_6$H$_4$ | C$_6$H$_5$ | 74 | 0.40; 0.31$^b$ 216; 149 —; — | Z: 1.2–2.1 (m,3H), 2.4–2.6 (m,5H), 4.2 (mc,1H), 4.9 (mc,1H), 5.7 (mc,1H), 6.6 (d,J=10Hz,1H), 7.1 (mc,2H), 7.4–7.6 (m,6H), 8.0 (mc,2H), E: 1.7 (mc,1H), 1.9 (mc,2H), 2.6–2.8 (m,5H), 4.3 (mc,1H), 5.2 (mc,1H), 5.5 (mc,1H), 6.6 (d,J=16Hz,1H), 7.1 (mc,2H), 7.3–7.5 (m,6H), 8.0 (mc, 2H). 403 (M+) |
| d | Id | CH | iC$_3$H$_7$ | 4-FC$_6$H$_4$ | CH$_3$ | 69 | —; 0,22$^c$ —; oil | E: 1.3 (d,J=7Hz, 6H); 1.5–1.8 (m,3H), 2.4–2.8 (m,5H), 3.3 (h,J=7Hz,1H), 4.2 (mc,1H), 5.2 (mc,1H), 5.3 (mc,1H), 6.6 (d,J=16Hz,1H), 6.9 |

TABLE 13-continued

Structure: lactone with HO group, connected via A=B (—CH=CH—) to a pyrimidine ring bearing R¹, R², R³, Z.

A—B = —CH=CH—

| Example | Compound | Z | R¹ | R² | R³ | Yield % | $R_f$ (Z; E) melting point °C. (Z; E) $[\alpha]_D^{25}$ (Z; E) | ¹H NMR: δ/ppm = MS: m/e = |
|---|---|---|---|---|---|---|---|---|
| | | | | | | | | (s,1H), 7.0-7.3 (m,4H). 368 (M⁺ + H) |
| e | Ie | CH | iC₃H₇ | 4-FC₆H₄ | C₆H₅ | 63 | —; — —; 0.22ᶜ | E: 1.4 (d, J=7Hz, 6H), 1.5 (brs,1H), 1.6 (mc,1H), 1.8-1.9 (m,1H), 2.6-2.8 (m,2H), 3.4 (h,J=7Hz,1H), 4.3 (mc,1H), 5.2 (mc,1H), 5.4 (mc,1H), 6.7 (d,J= 16Hz,1H), 7.1 (mc,2H), 7.3-7.5 (m,6H), 8.1 (mc,2H). |
| | | | | | | | —; oil | 431 (M⁺) |
| f | If | CH | 4-FC₆H₄ | iC₃H₇ | C₆H₅ | 70 | —; +25° (CH₃OH) —; 0.15ᶜ | E: 1.5 (d,J=7Hz, 6H), 1.5-1.8 (m,3H), 2.5-2.7 (m,2H), 3.4 (h,J=7Hz,1H), 4.3 (mc,1H), 5.2 (mc, 1H), 5.4 (mc,1H), 6.7 (d,J=16Hz,1H), 7.0-8.2 (m,10H) |
| | | | | | | | —; oil | 431 (M⁺) |
| g | Ig | CH | tC₄H₉ | 4-FC₆H₄ | C₆H₅ | 64 | —; — —; 0,27ᶜ | E: 1.5 (s,9H), 1.5-2.8 (m,5H), 4.2 (mc,1H), 5.2 (mc,1H), 5.5 (mc, 1H), 6.7 (d,J=16Hz, 1H), 7.0-7.6 (m,8H), 8.0-8.2 (m,2H) |
| | | | | | | | —; oil | 445 (M⁺) |
| h | Ih | CH | iC₃H₇ | 4-CH₃OC₆H₄ | C₆H₅ | 77 | —; — —; 0.26ᶜ | E: 1.5 (d,J=7Hz,6H), 1.4-1.8 (m,3H), 2.5-2.8 (m,2H), 3.6 (h, J=7Hz,3H), 3.9 (s, 3H), 4.3 (mc,1H), 5.2 (mc,1H), 5.5 (mc,1H), 6.7 (d,J= 16Hz,1H), 7.0-7.6 (m,8H), 8.1-8.2 (m,2H) |
| | | | | | | | —; oil | 443 (M⁺) |
| i | Ii | CH | iC₃H₇ | 4-FC₆H₄ | 2,5-(CH₃)₂C₆H₃ | 71 | —; — —; 0.30ᶜ | E: 1.3 (d,J=7Hz,6H), 1.5-1.8 (m,3H), 2.3 (s,3H), 2.4 (s,3H), 2.6-2.8 (m,2H), 3.5 (h,J=7Hz,1H), 4.3 (mc,1H), 5.2 (mc,1H), 5.5 (mc,1H), 6.6 (d, J=16Hz,1H), 6.9-7.5 (m,8H), |
| | | | | | | | —; oil | 459 (M⁺) |
| j | Ij | CH | iC₃H₇ | 4-F—C₆H₄ | 4-FC₆H₄ | 65 | —; — —; 0.20ᶜ | E: 1.4 (d, J=7Hz, 6H), 1.5-1.9 (m, 3H), 2.6-2.8 (m, 2H), 3.5 (h,J= 7Hz,1H), 4.3 (mc, 1H), 5.2 (mc,1H), 5.5 (mc,1H), 6.7 (d,J=16Hz,1H), 7.0-8.1 (m,9H) |
| | | | | | | | —; oil | |

TABLE 13-continued

A—B = —CH=CH—

| Example | Compound | Z | R¹ | R² | R³ | Yield % | $R_f$ (Z; E) melting point °C. (Z; E) $[\alpha]_D^{25}$ (Z; E) | ¹H NMR: δ/ppm = MS: m/e = |
|---|---|---|---|---|---|---|---|---|
| k | Ik | N | CH₃ | 4-FC₆H₄ | CH₃ | 83 | 0.12; 0.14$^d$<br>—; 174–176<br>—; +21° (CH₃OH) | 449 (M⁺)<br>E: 1.6 (s,1H), 1.6–2.0 (m,2H), 2.6–2.8 (m,8H), 4.4 (mc,1H), 5.3 (mc,1H), 5.6 (mc,1H), 6.6 (mc,1H), 7.0–7.2 (mc,2H), 7.5–7.6 (m,2H), |
| l | Il | N | CH₃ | 4-ClC₆H₄ | CH₃ | 91 | 0.16; 0.18$^d$<br>—; oil<br>—; — | E: 1.5–2.0 (brs, 1H), 1.7–2.1 (m, 2H), 2.6–2.9 (m,8H), 4.4 (mc,1H), 5.2 (mc,1H), 5.1 (mc, 1H), 6.6 (mc,1H), 7.4–7.6 (m,4H). |
| m | Im | N | CH₃ | cC₆H₁₁ | CH₃ | 92 | 0.12; 0.13<br>oil: oil<br>—; — | |
| n | In | N | CH₃ | 4-ClC₆H₄ | H | | 0.14; 0.16$^d$<br>oil; oil<br>—; — | 330 (M⁺) |
| o | Io | N | iC₃H₇ | 4-FC₆H₄ | C₆H₅ | 93 | —; 0.10$^d$<br>—; 164–166 | 344 (M⁺)<br>1.5 (d, J=7Hz, 6H), 1.6 (s,1H), 1.7–2.0 (m,2H), 2.6–2.9 (m,2H), 3.4 (h,J=7Hz,1H), 4.3 (mc,1H), 5.3 (mc,1H), 5.6 (mc, 1H), 6.8 (dd,J= 16Hz,1Hz,1H), 7.2–7.7 (m,7H), 8.6 (mc,2H) |
| p | Ip | N | iC₃H₇ | 4-FC₆H₄ | CH₃ | 70 | —; +14 (CH₃OH)<br>—; 0.17$^b$<br>—; oil<br>—; — | |
| q | Iq | CH | iC₃H₇ | 4-FC₆H₄ | iC₃H₇ | 71 | —; —<br>—; 137–140<br>—; — | 370 (M⁺)<br>1.2–1.3 (m,12H), 1.5–1.7 (m,2H), 1.8 (mc,1H), 2.5–2.8 (m,2H), 3.0 (h,J=7Hz,1H), 3.3 (h,J=7Hz,1H), 4.2 (mc,1H), 5.1 (mc, 1H), 5.3 (mc,1H), 6.6 (dd,J=16Hz,1Hz, 1H), 7.1 (mc,2H), 7.3(mc,2H) |
| r | Ir | CH | iC₃H₇ | 4-FC₆H₄ | tC₄H₄ | 78 | —; 0.35$^c$<br>—; 158–160<br>—; +26.4° (CH₃OH) | 398 (M⁺ + H)<br>1.3 (mc,6H), 1.4 (s,9H), 1.5–1.7 (m 3H), 1.8 (mc,1H), 2.6 (mc,1H), 2.7 (mc,1H), 3.3 (h,J= 7Hz,3H), 4.3 (mc, 1H), 5.2 (mc,1H), 5.4 (dd,J=16Hz,6Hz, 1H), 6.6 (dd,J= 16Hz,1Hz,1H), 7.0 (s,1H), 7.1 (mc, |

TABLE 13-continued

A—B = —CH=CH—

| Example | Compound | Z | R¹ | R² | R³ | Yield % | $R_f$ (Z; E) melting point °C. (Z; E) $[\alpha]_D^{25}$ (Z; E) | ¹H NMR: δ/ppm = MS: m/e = |
|---|---|---|---|---|---|---|---|---|
| s | Is | CH | iC₃H₇ | 4-FC₆H₄ | cC₆H₁₁ | 65 | —; 0.30$^c$<br>—; 135–138<br>—; — | 2H), 7.3 (mc,2H) 412 (M⁺ + H) 1.2 (mc,6H), 1.3–2.0 (m,14H), 2.6 (mc,1H), 2.7 (mc,1H), 3.3 (h,J=7Hz,1H), 4.2 (mc,1H), 5.1 (mc,1H), 5.3, (dd,J=16Hz,5Hz,1H), 6.6 (dd,J=16Hz,1Hz,1H), 6.8 (s,1H), 7.1 (mc,2H), 7.2 (mc,2H) |
| t | It | CH | C₂H₅ | 4-FC₆H₄ | C₆H₅ | 53 | 0.20; 0.15$^c$<br>oil; oil<br>—; — | 1.4 (mc,6H), 1.6–1.9 (m,2H), 2.4–2.8 (m,2H), 2.9 (q, J=7Hz,2H), 4.2 (mc,1H), 4.8 (mc,1H), 5.6 (dd, J=10Hz,6H,1H), 6.7 (d,J=10Hz,1H), 7.1–7.2 (m,2H), 7.3–7.5 (m,6H), 8.0–8.1 (m,2H), E: 1.3 (mc,3H), 1.4 (mc,6H), 1.6–1.9 (m,2H), 2.4–2.8 (m,2H), 3.0 (q,J=7Hz,2H), 4.3 (mc,1H), 5.2 (mc,1H), 5.4 (dd,J=16Hz,6Hz,1H), 6.6 (dd,J=16Hz,1Hz,1H), 7.1–7.2 (mc,2H), 7.3–7.5 (m,6H), 8.0–8.1 (m,2H) 418 (M⁺ + H) |
| u | Iu | CH | cC₆H₁₁ | 4-FC₆H₄ | C₆H₅ | 45 | —; 0.32$^f$<br><br>—; 196–198<br>—; — | 1.3–2.0 (m,13H), 2.6 (mc,1H), 2.7 (mc,1H), 3.0 (mc,1H), 4.3 (mc,1H), 5.2 (mc,1H), 5.4 (mc,1H), 6.7 (dd, J=16Hz,1Hz,1H), 7.0 (mc,2H), 7.3–7.5 (m,6H), 8.1 (mc,2H) 472 (M⁺ + H) |
| v | Iv | N | iC₃H₇ | 4-FC₅H₄ | iC₃H₇ | 71 | —; 0.16$^e$<br><br>—; oil | 1.3 (d,6H), 1.5 (d, 6H), 1.5–1.9 (m,2H), 2.6–2.8 (m,2H), 3.2 u. 3.32 (h,1H), 4.3 (m,1H), 5.25 (m,1H), 5.5 (dd,1H), 6.7 (dd, J=16Hz,1Hz,1H), 7.1–7.5 (m,4H) 399 (M⁺ + H) |
| w | Iw | N | iC₃H₇ | 4-FC₆H₄ | 4-FC₆H₄ | 48 | —; 0.24$^e$ | 1.48 (d,6H), 1.5–2.0 (m,2H), 2.6–2.8 (m,2H), 3.40 (h,1H), 4.35 (m, |

TABLE 13-continued

A—B = —CH=CH—

| Example | Compound | Z | R¹ | R² | R³ | Yield % | $R_f$(Z; E) melting point °C. (Z; E) $[\alpha]_D^{25}$(Z; E) | ¹H NMR: δ/ppm = MS: m/e = |
|---|---|---|---|---|---|---|---|---|
| aa | Iaa | CH | iC₃H₇ | 4-HOC₆H₄ | C₆H₅ | — | —; 138–140 0.45$^d$ | 1H), 5.25 (m,1H), 5.55 (dd,J=16Hz, 1H), 6.78 (dd,J= 16Hz,1Hz,1H), 7.15– 7.6 (m,4H) 1.6–1.9 (m,2H), 2.6 (mc,1H), 2.7 (mc,1H), 3.4 (h,J= 7Hz,1H), 4.2 (mc, 1H), 5.2 (mc,1H), 5.4 (dd,J=16Hz,6H, 1H), 6.7 (dd,J= 16Hz,1Hz,1H), 6.9 (mc,2H), 7.2 (mc, 2H), 7.4–7.5 (m, 3H), 7.5 (s,1H), 8.1 (mc,2H) |
| ab | Iab | CH | iC₃H₇ | 4-FC₆H₄ | 4-HOC₆H₄ | — | 180–182 0.22$^e$ | 430 (M⁺ + H) 1.3 (mc,6H), 1.5 (brs,2H), 1.6 (mc, 1H), 1.8 (mc,1H), 2.6 (mc,1H), 2.7 (mc,1H), 3.5 (h, J=7Hz,1H), 4.3 (mc, 1H), 5.2 (mc,1H), 5.4 (dd,J=16Hz,6Hz, 1H), 6.7 (dd,J= 16Hz,1Hz,1H), 6.9 (mc,2H), 7.1 (mc, 2H), 7.3 (mc,2H), 7.4 (s,1H), 8.0 (mc,2H) |
| ac | Iac | CH | cC₃H₅ | 4-FC₆H₄ | C₆H₅ | — | 185–187(decomp.) 0.20$^c$ | 448 (M⁺ + H) 1.0 (mc,2H), 1.3 (mc,2H), 1.6–1.9 (m,2H), 2.6 (mc, 1H), 2.7 (mc,1H), 4.2 (mc,1H), 5.2 (mc,1H), 5.4 (dd, J=16Hz,6Hz,1H), 6.7 (dd,J=16Hz,1Hz, 1H), 7.1 (mc,2H), 7.3–7.5 (m,6H), 8.0 (mc,2H) |
|  |  |  |  |  |  |  | oil | 430 (M⁺ + H) |

$^a$Ethyl acetate/methanol 10:1
$^b$Cyclohexane/ethyl acetate 1:4
$^c$Cyclohexane/ethyl acetate 2:1
$^d$Ethyl acetate
$^e$Cyclohexane/ethyl acetate 1:1
$^f$Cyclohexane/ethyl acetate 4:1

EXAMPLE 12

Hydrogenation of compounds of the general formula I with A—B=—CH=CH— to give compounds of the formula I with A—B=—CH₂—CH₂—

EXAMPLE 12a (4R,6S)-(6-(2-(2,6-Dimethyl-4-(4-fluorophenyl)-pyrimidin-3-yl)ethyl)-4-hydroxy-3,4,5,6-tetrahydro-2H-pyran-2-one (Ix) (R¹=CH₃, R²=4-FC₆H₄, R³=CH₃, Z=N, A—B=—CH₂—CH₂)

4.00 g (11.7 mmol) of the compound E-Ik were dissolved in a mixture of 50 ml of methanol and 50 ml of ethyl acetate and, after addition of 50 mg of palladium on charcoal/10% and of 50 μl of triethylamine, the mixture was shaken in a hydrogen atmosphere until no more H₂ was absorbed. The reaction solution was filtered through kieselguhr and evaporated. Ix remained in the form of white crystals.

Yield: 3.93 g (98%).
Melting point: 170°-172° C.
$[\alpha]_D^{25}(CH_3OH): +13°$.
1H-NMR: δ/ppm=1.5-1.9 (m,2H), 1.9 (brs,1H), 2.6 (s,3H), 2.7 (s,3H), 2.6-3.0 (m,2H), 4.3 (m,1H), 4.5-4.6 (m,1H), 7.1-7.2 (m,2H), 7.4-7.5 (m,2H).

EXAMPLE 12b 1.0 g of the compound E-Ie (Example 11e) was reacted under the conditions indicated in Example 12a to give the hydrogenation product Iy. ($R^1$=iC$_3$H$_7$, $R^2$=4-FC$_6$H$_4$, $R^3$=C$_6$H$_5$, Z=CH, A—B=—CH$_2$—CH$_2$).

Yield: 0.91 g (91%).
Melting point: oil.
$[\alpha]_D^{25}(CH_3OH): +26°$.
1H-NMR: δ/ppm=1.3-1.8 (m,11H), 2.3-2.8 (m,7H), 3.4 (h,J=7 Hz,1H), 4.2 (mc,1H), 4.5 (mc,1H), 7.1 (mc,2H), 7.3-7.5 (m,6H), 8.1 (mc,2H)
MS: m/e=433 (M+).

EXAMPLE 12c 1.0 g of the compound E-It (Example 11t) was reacted under the conditions indicated in Example 12a to give the hydrogenation product Iz. ($R^1$=C$_2$H$_5$, $R^2$=4-FC$_6$H$_4$, $R^3$=C$_6$H$_5$, Z=CH, A—B=—CH$_2$—CH$_2$).

Yield: 0.93 g (91%).
Melting point: 53°-55° C.
1H-NMR: δ/ppm=1.4 (mc,6H), 1.5-1.9 (m,4H), 2.5-2.9 (m,4H), 4.3 (mc,1H), 4.5 (mc,1H), 7.1 (mc,2H), 7.3-7.5 (m, 6H), 8.0 (mc,2H)
MS: m/e=429 (M+).

It is possible in a manner analogous to that described in Example 12 to hydrogenate the compounds of the general formula I with A—B=—CH=CH— to give compounds of the general formula I with A—B=—CH$_2$—CH$_2$—.

EXAMPLE 13

Preparation of the salts of the free dihydroxy acids of the general formula II

Example 13a ($R^1$=CH$_3$, $R^2$=4-FC$_6$H$_4$, $R^3$=CH$_3$, $R^4$=K, Z=CH, A—B=(E)—CH=CH—)

(E)- and (Z)-(3R,5S)-3,5-Dihydroxy-7-(2,6-dimethyl-4-(4-fluorophenyl)pyridin-3-yl)-6-heptenoic acid potassium salts E-IIa and Z-IIa (as 30:70 mixture of Z and E isomers)

0.10 g (0.29 mmol) of the compound Ia was dissolved in 5 ml of ethanol. 2.9 ml (0.29 mmol) of a 0.1-molar solution of potassium hydroxide in ethanol was added to this solution at room temperature. The progress of the reaction was followed by thin-layer chromatography (mobile phase ethyl acetate/methanol 10:1). Precursor was no longer present after 3 h. The reaction solution was concentrated in vacuo. The potassium salt IIa remained in the form of white crystals.

Yield: 0.11 g (96%) (30:70 mixture of Z-IIa and E-IIa)

The isomers were then separated by medium pressure liquid chromatography.

Z-IIa: Rf (ethyl acetate/methanol 2:1): 0.23.
IR: 1605/1575 cm$^{-1}$ (C=O band).
E-IIa: Rf (ethyl acetate/methanol 2:1) 0.19.
IR: 1610/1580 cm$^{-1}$ (C=O band).

EXAMPLES 13b–13z

The compounds IIb–IIz were prepared in a manner analogous to that described in Example 13a (cf. Table 14).

TABLE 14

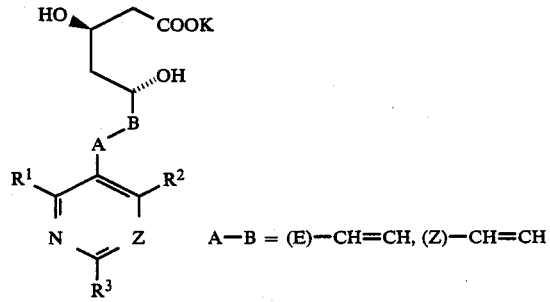

A—B = (E)—CH=CH, (Z)—CH=CH

| Example | Compound | Z | R$^1$ | R$^2$ | R$^3$ | Yield % | R$_f$(Z; E) |
|---|---|---|---|---|---|---|---|
| b | IIb | CH | CH$_3$ | 4-ClC$_6$H$_4$ | CH$_3$ | 95 | 0.25; 0.23$^a$ |
| c | IIc | CH | CH$_3$ | 4-FC$_6$H$_4$ | CH$_3$ | 97 | 0.30; 0.26$^a$ |
| d | IId | CH | iC$_3$H$_7$ | 4-FC$_6$H$_4$ | CH$_3$ | 92 | —; 0.29$^a$ |
| e | IIe | CH | iC$_3$H$_7$ | 4-FC$_6$H$_4$ | C$_6$H$_5$ | 99 | —; 0.44$^a$ |
| f | IIf | CH | 4-FC$_6$H$_4$ | iC$_3$H$_7$ | C$_6$H$_5$ | 91 | —; 0.38$^a$ |
| g | IIg | CH | tC$_4$H$_9$ | 4-FC$_6$H$_4$ | C$_6$H$_5$ | 97 | —; 0.50$^a$ |
| h | IIh | CH | iC$_3$H$_7$ | 4-CH$_3$OC$_6$H$_4$ | C$_6$H$_5$ | 96 | —; 0.47$^a$ |
| i | IIi | CH | iC$_3$H$_7$ | 4-FC$_6$H$_4$ | 2,5-(CH$_3$)$_2$C$_6$H$_3$ | 100 | —; 0.56$^a$ |
| j | IIj | CH | iC$_3$H$_7$ | 4-FC$_6$H$_4$ | 4-FC$_6$H$_4$ | 94 | —; 0.40$^a$ |
| k | IIk | N | CH$_3$ | 4-FC$_6$H$_4$ | CH$_3$ | 94 | 0.20; 0.16$^a$ |
| l | IIl | N | CH$_3$ | 4-ClC$_6$H$_4$ | CH$_3$ | 97 | 0.17; 0.13$^a$ |
| m | IIm | N | CH$_3$ | cC$_6$H$_{11}$ | CH$_3$ | 96 | 0.32; 0.27$^a$ |
| n | IIn | N | CH$_3$ | 4-ClC$_6$H$_4$ | H | 93 | 0.20; 0.15$^a$ |
| o | IIo | N | iC$_3$H$_7$ | 4-FC$_6$H$_4$ | C$_6$H$_5$ | 97 | —; 0.35$^a$ |
| p | IIp | N | iC$_3$H$_7$ | 4-FC$_6$H$_4$ | CH$_3$ | 93 | —; 0.31$^a$ |
| q | IIq | CH | iC$_3$H$_7$ | 4-FC$_6$H$_4$ | iC$_3$H$_7$ | 95 | —; 0.49$^a$ |
| r | IIr | CH | iC$_3$H$_7$ | 4-FC$_6$H$_4$ | tC$_4$H$_9$ | 98 | —; 0.53$^a$ |
| s | IIs | CH | iC$_3$H$_7$ | 4-FC$_6$H$_4$ | cC$_6$H$_{11}$ | 96 | —; 0.50$^a$ |
| t | IIt | CH | C$_2$H$_5$ | 4-FC$_6$H$_4$ | C$_6$H$_5$ | 98 | 0.40; 0.36$^a$ |
| u | IIu | CH | cC$_6$H$_{11}$ | 4-FC$_6$H$_4$ | C$_6$H$_5$ | 100 | —; 0.64$^a$ |
| v | IIv | N | iC$_3$H$_7$ | 4-FC$_6$H$_4$ | iC$_3$H$_7$ | 100 | —; 0.26$^b$ |
| w | IIw | N | iC$_3$H$_7$ | 4-FC$_6$H$_4$ | 4-FC$_6$H$_4$ | 100 | —; 0.11$^b$ |

TABLE 14-continued

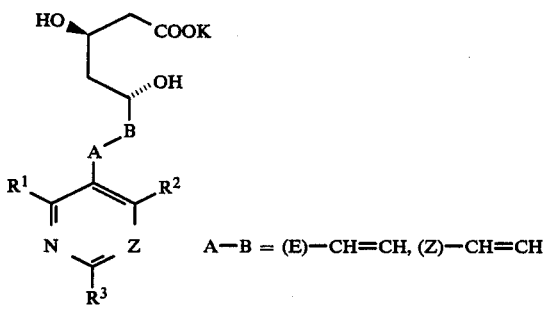

A—B = (E)—CH=CH, (Z)—CH=CH

| Example | Compound | Z | R¹ | R² | R³ | Yield % | $R_f$(Z; E) |
|---|---|---|---|---|---|---|---|
| x | IIx<br>A—B=CH₂—CH₂ | N | CH₃ | 4-FC₆H₄ | CH₃ | 99 | —; 0.24$^a$ |
| y | IIy<br>A—B=CH₂—CH₂ | CH | iC₃H₇ | 4-FC₆H₄ | C₆H₅ | 98 | —; 0.29$^a$ |
| z | IIz<br>A—B=CH₂—CH₂ | CH | C₂H₅ | 4-FC₆H₄ | C₆H₅ | 96 | —; 0.20$^a$ |
| aa | IIaa | CH | iC₃H₇ | 4-HOC₆H₄ | C₆H₅ | 69 | —; 0.30$^a$ |
| ab | IIab | CH | iC₃H₇ | 4-FC₆H₄ | 4-HOC₆H₄ | 83 | —; 0.18$^a$ |
| ac | IIac | CH | cC₃H₇ | 4-FC₆H₄ | C₆H₅ | 96 | —; 0.40$^a$ |

$^a$Ethyl acetate/methanol 2:1
$^b$Dichloromethane/methanol 9:1

EXAMPLE 14

General procedure for the preparation of carboxylic esters of the free dihydroxy acids of the general formula II Example 14a (R¹=CH₃, R²=4-FC₆H₄, R³=CH₃, R⁴=CH₃, Z=CH, A—B=(E)—CH=CH)

Methyl E-(3R,5S)-3,5-dihydroxy-7-(2,6-dimethyl-4-(4-fluorophenyl)pyridin-3-yl)-6-heptenoate E-IIad 0.40 g (1.17 mmol) of the compound E-Ia (Example 11) was dissolved in 10 ml of methanol and, at room temperature 1.3 ml (0.13 mmol) of a 0.1 molar solution of sodium methanolate in methanol were added. After stirring for 1 hour—the reaction conversion was followed by thin-layer chromatography (mobile phase ethyl acetate)—the solvent was removed in vacuo. The residue was taken up in water, and the mixture was neutralized with acetic acid and extracted with ether. The organic extracts were dried over magnesium sulfate and evaporated. 0.39 g (94%) of the title compound E-IIad remained.

¹H-NMR (detail); δ/ppm=3.6 (s,3H).

The methyl esters of the free dihydroxy acids of the general formula II can be prepared in a manner analogous to that described in Example 14a. It is also possible, by replacing methanol by other alcohols (R⁴OH), easily to prepare other corresponding esters II (R⁴=ethyl, isopropyl, benzyl etc).

We claim:

1. A 3-Demethylmevalonic acid derivative of the formula I (δ-lactone) or II (corresponding dihydroxy carboxylic acid derivative)

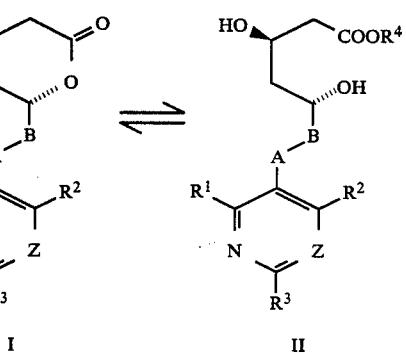

in which

A—B denotes a radical of the formula —CH=CH— or —CH₂—CH₂—,

Z denotes a radical of the formula —CH,

R¹, R² and R³, independently of one another, denote hydrogen, a saturated or unsaturated, straight-chain or branched hydrocarbon radical which has up to 6 carbon atoms and can optionally be substituted on the terminal carbon by a saturated or unsaturated, cyclic hydrocarbon radical having 3–6 carbon atoms, a cyclic hydrocarbon radical which has 3–7 carbon atoms and is saturated or is unsaturated once or twice, an aromatic radical selected from the group consisting of phenyl, furyl, thienyl and pyridinyl, which can optionally carry in the nucleus 1–3 identical or different substituents from the following groups: halogen, trifluoromethyl, alkyl or alkenyl, each having up to 6 carbon atoms, hydroxyl, alkoxy having 1–6 carbon atoms, carboxyl, or carbalkoxy having 1–6 carbon atoms in the alkoxy moiety, R⁴ denotes hydrogen, a straight-chain or branched, saturated or unsaturated hydrocarbon radical having up to 5 carbon atoms, a benzyl radical whose nucleus can be substituted 1–2 times by halogen or an alkyl radical having 1–4 carbon atoms, an alkali metal or an ammonium ion NR$^5$R$^6$R$^7$R$^8$, where R$^5$, R$^6$, R$^7$ and R$^8$ are identical or different and denote hydrogen, alkyl having 1-4 carbon atoms or hydroxyalkyl having 1-4 carbon atoms.

2. A compound as claimed in claim 1, wherein, in formula I or formula II,

R$^1$ and R$^2$, independently of one another, denote a straight-chain or branched alkyl radical having 1 to 4 carbon atoms, a cycloalkyl radical having 3-6 carbon atoms, a cycloalkylmethyl or cycloalkenylmethyl radical having a ring size of 5-6 carbon atoms, a phenyl radical which can optionally carry 1-3 identical or different substituents from the following groups halogen, trifluoromethyl, alkyl having 1-4 carbon atoms, hydroxyl, alkoxy having 1-4 carbon atoms or carbalkoxy having 1-4 carbon atoms in the alkoxy moiety, R$^3$ represents hydrogen, a straight-chain or branched alkyl or alkenyl radical having up to 6 carbon atoms, a cycloalkyl or-alkenyl radical, each having 3-6 carbon atoms, a phenyl or pyridinyl radical, it being possible for the aromatic radicals optionally to carry 1-3 identical or different substituents from the following groups halogen, alkyl having 1-4 carbon atoms, hydroxyl, alkoxy having 1-4 carbon atoms or carbalkoxy having 1-4 carbon atoms in the alkoxy moiety, R$^4$ is hydrogen, methyl, ethyl, isopropyl, isobutyl, benzyl, sodium, potassium, ammonium (NH$_4$) or methyltris(hydroxymethyl)ammonium.

3. A compound as claimed in claim 1, wherein, in formula I and formula II

R$^1$ represents methyl, ethyl, isopropyl, sec.-butyl, tert.-butyl, cyclopropyl, cyclohexyl, phenyl, 4-chlorophenyl, 4-fluorophenyl, 4-hydroxyphenyl, 4-methoxyphenyl, 4-fluoro-3-methylphenyl, 3,5-dimethylphenyl, cyclohexylmethyl or 4-trifluoromethyl, R$^2$ represents methyl, ethyl, isopropyl, sec.-butyl, tert.-butyl, cyclopropyl, cyclohexyl, phenyl, 4-chlorophenyl, 4-fluorophenyl, 4-hydroxyphenyl, 4-methoxyphenyl, 4-fluoro-3-methylphenyl, 3,5-dimethylphenyl, cyclohexylmethyl, 4-trifluoromethyl, R$^3$ represents hydrogen, methyl, isopropyl, tert.-butyl, cyclohexyl, phenyl, 4-fluorophenyl, 4-hydroxyphenyl, 2,5-dimethylphenyl, 3,5-dimethylphenyl or 4-trifluoromethylphenyl, R$^4$ represents hydrogen, methyl, ethyl, sodium or potassium.

4. A compound as claimed in claim 1, wherein, in formula I and formula II,

Z represents the CH group,

R$^1$ represents ethyl, isopropyl, cyclopropyl,

R$^2$ represents 4-fluorophenyl, 4-hydroxyphenyl,

R$^3$ represents isopropyl, tert.-butyl, cyclohexyl, phenyl, 4-fluorophenyl or 4-hydroxyphenyl and R$^4$ represents sodium or potassium.

5. A compound of the formula V

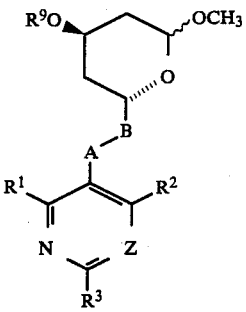

in which

A—B denotes a radical of the formula —CH=CH— or —CH$_2$—CH$_2$—,

Z denotes a radical of the formula —CH,

R$^1$, R$^2$ and R$^3$, independently of one another, denote hydrogen, a saturated or unsaturated, straight-chain or branched hydrocarbon radical which has up to 6 carbon atoms and can optionally be substituted on the terminal carbon by a saturated or unsaturated, cyclic hydrocarbon radical having 3-6 carbon atoms, a cyclic hydrocarbon radical which has 3-7 carbon atoms and is saturated or is unsaturated once or twice, an aromatic radical selected from the group consisting of phenyl, furyl, thienyl and pyridinyl, which can optionally carry in the nucleus 1-3 identical or different substituents from the following groups: halogen, trifluoromethyl, alkyl or alkenyl, each having up to 6 carbon atoms, hydroxyl, alkoxy having 1-6 carbon atoms, carboxyl, or carbalkoxy having 1-6 carbon atoms in the alkoxy moiety, and R$^9$ is a protective group which is stable to bases and weak acids.

6. A compound of the formula VI

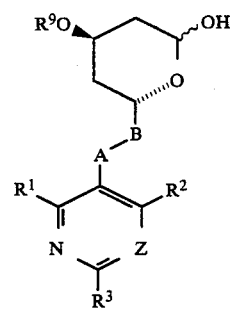

in which

A—B denotes a radical of the formula —CH=CH— or —CH$_2$—CH$_2$—,

Z denotes a radical of the formula —CH,

R$^1$, R$^2$ and R$^3$, independently of one another, denote hydrogen, a saturated or unsaturated, straight-chain or branched hydrocarbon radical which has up to 6 carbon atoms and can optionally be substituted on the terminal carbon by a saturated or unsaturated, cyclic hydrocarbon radical having 3-6 carbon atoms, a cyclic hydrocarbon radical which has 3-7 carbon atoms and is saturated or is unsaturated once or twice, an aromatic radical selected from the group consisting of phenyl, furyl, thienyl and pyridinyl, which can optionally carry in the nucleus 1-3 identical or different substituents from the following groups: halogen, trifluoromethyl, alkyl or alkenyl, each having up to 6 carbon atoms, hydroxyl, alkoxy having 1-6 carbon atoms, carboxyl, or carbalkoxy having 1-6 carbon atoms in the alkoxy moiety, and $R^9$ is a protective group which is stable to bases and weak acids.

7. A compound of the formula VII

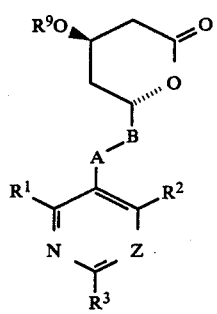

in which

A—B denotes a radical of the formula —CH=CH— or —CH$_2$—CH$_2$—,

Z denotes a radical of the formula —CH, $R^1$, $R^2$ and $R^3$, independently of one another, denote hydrogen, a saturated or unsaturated, straight-chain or branched hydrocarbon radical which has up to 6 carbon atoms and can optionally be substituted on the terminal carbon by a saturated or unsaturated, cyclic hydrocarbon radical having 3-6 carbon atoms, a cyclic hydrocarbon radical which has 3-7 carbon atoms and is saturated or is unsaturated once or twice, an aromatic radical selected from the group consisting of phenyl, furyl, thienyl and pyridinyl, which can optionally carry in the nucleus 1-3 identical or different substituents from the following groups: halogen, trifluoromethyl, alkyl or alkenyl, each having up to 6 carbon atoms, hydroxyl, alkoxy having 1-6 carbon atoms, carboxyl, or carbalkoxy having 1-6 carbon atoms in the alkoxy moiety, and $R^9$ is a protective group which is stable to bases and weak acids.

8. A pharmaceutical composition for the treatment or prophylaxis of arteriosclerosis or hypercholesterolemia which comprises an effective amount for said treatment of a compound of the formula I or II as claimed in claim 1, together with a pharmaceutically acceptable carrier.

9. A method for the treatment or prophylaxis of arteriosclerosis or hypercholesterolemia in a patient which comprises administering to the patient an effective amount of a compound of the formula I or II as claimed in claim 1.

* * * * *